United States Patent
Mills et al.

(10) Patent No.: US 10,072,293 B2
(45) Date of Patent: Sep. 11, 2018

(54) SYSTEMS, MODELS AND METHODS FOR IDENTIFYING AND EVALUATING SKIN-ACTIVE AGENTS EFFECTIVE FOR TREATING DANDRUFF/SEBORRHEIC DERMATITIS

(75) Inventors: Kevin John Mills, Goshen, OH (US); Robert Lloyd Binder, Montgomery, OH (US); Robert Scott Youngquist, Mason, OH (US); Jun Xu, Mason, OH (US); Ping Hu, Mason, OH (US); Makio Tamura, Cincinnati, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

(21) Appl. No.: 13/437,072

(22) Filed: Apr. 2, 2012

(65) Prior Publication Data

US 2012/0258074 A1    Oct. 11, 2012

Related U.S. Application Data

(60) Provisional application No. 61/470,131, filed on Mar. 31, 2011, provisional application No. 61/488,501, filed on May 20, 2011, provisional application No. 61/519,504, filed on May 24, 2011.

(51) Int. Cl.
*G01N 33/48* (2006.01)
*C12Q 1/6883* (2018.01)

(52) U.S. Cl.
CPC ..... *C12Q 1/6883* (2013.01); *C12Q 2600/136* (2013.01); *C12Q 2600/148* (2013.01); *C12Q 2600/158* (2013.01)

(58) Field of Classification Search
CPC .................................................. C12Q 1/6883
USPC ......................................................... 702/19
See application file for complete search history.

(56) References Cited

U.S. PATENT DOCUMENTS

| | | | |
|---|---|---|---|
| 2,694,668 A | 11/1954 | Fricke | |
| 2,809,971 A | 10/1957 | Bernstein | |
| 2,826,551 A | 3/1958 | Geen | |
| 3,152,046 A | 10/1964 | Kapral | |
| 3,236,733 A | 2/1966 | Karsten | |
| 3,694,668 A | 9/1972 | Foerster | |
| 3,753,196 A | 8/1973 | Kurtz | |
| 3,755,560 A | 8/1973 | Dickert et al. | |
| 3,761,418 A | 9/1973 | Parran | |
| 3,964,500 A | 6/1976 | Drakoff | |
| 4,089,945 A | 5/1978 | Brinkman | |
| 4,323,683 A | 4/1982 | Bolich, Jr. | |
| 4,345,080 A | 8/1982 | Bolich, Jr. | |
| 4,364,837 A | 12/1982 | Pader | |
| 4,379,753 A | 4/1983 | Bolich, Jr. | |
| 4,421,769 A | 12/1983 | Dixon | |
| 4,470,982 A | 9/1984 | Winkler | |
| 4,677,120 A | 6/1987 | Parish | |
| 4,741,855 A | 5/1988 | Grote | |
| 4,885,107 A | 12/1989 | Wetzel | |
| 4,885,311 A | 12/1989 | Parish et al. | |
| 4,967,341 A | 10/1990 | Yamamoto | |
| 5,049,584 A | 9/1991 | Purcell et al. | |
| 5,104,646 A | 4/1992 | Bolich, Jr. et al. | |
| 5,106,609 A | 4/1992 | Bolich, Jr. et al. | |
| 5,124,356 A | 6/1992 | Purcell et al. | |
| RE34,075 E | 9/1992 | Purcell et al. | |
| 5,297,279 A | 3/1994 | Bannon | |
| 5,624,666 A | 4/1997 | Coffindaffer | |
| D391,162 S | 2/1998 | Kokenge | |
| 6,451,300 B1 | 9/2002 | Dunlop | |
| 6,641,848 B1 | 11/2003 | Bonte et al. | |
| 6,872,401 B2 | 3/2005 | Seyler et al. | |
| 6,974,569 B2 | 12/2005 | Dunlop | |
| 7,001,594 B1 | 2/2006 | Peffly | |
| D516,436 S | 3/2006 | Campbell et al. | |
| 7,101,889 B2 | 9/2006 | Kaczvinsky, Jr. | |
| D535,191 S | 1/2007 | Corker | |
| D542,660 S | 5/2007 | Thomas et al. | |
| D547,193 S | 7/2007 | Blasko et al. | |
| D547,661 S | 7/2007 | Blasko et al. | |
| D558,591 S | 1/2008 | Blasko et al. | |
| D563,221 S | 3/2008 | Ashiwa et al. | |
| D570,707 S | 6/2008 | Blasko et al. | |
| 7,436,987 B2 | 10/2008 | Takano et al. | |
| 7,585,827 B2 | 9/2009 | Geary et al. | |

(Continued)

FOREIGN PATENT DOCUMENTS

| | | |
|---|---|---|
| CN | 101152138 A | 12/2010 |
| FR | 2811226 B1 | 6/2003 |

(Continued)

OTHER PUBLICATIONS

Lamore, S.D. "The topical antimicrobial zinc pyritliione is a heat shock response inducer that causes DNA damage and PARP-dependent energy crisis in human skin cells" Cell Stress Chaperones, (2010), 15, [3], p. 309-322.
Kerr, K. "Epidermal Changes Associated with Symptomatic Resolution of Dandruff: Biomarkers of Scalp Health" Int. J. Dermatol., (Jan. 2011), 50, p. 102-113.
International Search Report PCT/US2012/031509; dating Jul. 12, 2012; 19 pages.
G. Smith et al: "Regulation of cutaneous 1.2,5 drug-metabolizing enzymes and cytoprotective gene expression by topical drugs in human skin in vivo". British Journal of Dermatology, vol. 155, No. 2, Aug. 1, 2006 (Aug. 1, 2006), pp. 275-281.
Lamb Justin: "Innovation—The 7-15 Connectivity Map: a new tool for biomedical research" Nature Reviews. Cancer, Natur Publishing Group, London, GB, vol. 7, No. 1. Jan. 1, 2007.

(Continued)

*Primary Examiner* — Jerry Lin
(74) *Attorney, Agent, or Firm* — Linda M. Sivik

(57) ABSTRACT

Methods and systems for determining functional relationships between a skin-active agent and a skin condition of interest, and methods and systems for identifying cosmetic agents effective for treatment of dandruff, as well as the use of agents identified by such methods and systems for the preparation of cosmetic compositions, personal care products, or both are provided. Methods for developing in vitro models of skin disease and models for specific skin diseases are also provided.

22 Claims, 23 Drawing Sheets

(56) References Cited

U.S. PATENT DOCUMENTS

| | | |
|---|---|---|
| 7,653,491 B2 | 1/2010 | Schadt et al. |
| 7,654,420 B2 | 2/2010 | Honda et al. |
| 7,704,932 B2 | 4/2010 | Evans et al. |
| 7,709,015 B2 | 5/2010 | Masuda et al. |
| 7,727,516 B2 | 6/2010 | Botchkareva et al. |
| 7,772,214 B2 | 8/2010 | Vatter et al. |
| 7,815,948 B2 | 10/2010 | Paufique |
| 7,890,267 B2 | 2/2011 | Glinsky |
| 8,106,037 B2 | 1/2012 | Rubin et al. |
| 8,324,447 B2 | 12/2012 | Goldstein et al. |
| 8,535,738 B2 | 9/2013 | Collins et al. |
| 8,831,271 B2 | 9/2014 | Sese et al. |
| 9,434,993 B2 | 9/2016 | Binder et al. |
| 2002/0012927 A1 | 1/2002 | Burmer et al. |
| 2002/0044953 A1 | 4/2002 | Michelet et al. |
| 2002/0169562 A1 | 11/2002 | Stephanopoulos et al. |
| 2002/0197633 A1 | 12/2002 | Jones et al. |
| 2003/0088437 A1 | 5/2003 | Iobst et al. |
| 2003/0149347 A1 | 8/2003 | Kauffmann et al. |
| 2003/0170739 A1 | 9/2003 | Iobst et al. |
| 2003/0223951 A1 | 12/2003 | Geary et al. |
| 2004/0142335 A1 | 7/2004 | Petersohn et al. |
| 2005/0009015 A1 | 1/2005 | Ji et al. |
| 2005/0170378 A1 | 8/2005 | Yakhini et al. |
| 2007/0040306 A1 | 2/2007 | Morel et al. |
| 2007/0154425 A1 | 7/2007 | Potin |
| 2007/0155772 A1 | 7/2007 | Ide et al. |
| 2007/0184012 A1 | 8/2007 | Perrier et al. |
| 2007/0205226 A1 | 9/2007 | Honda et al. |
| 2008/0280844 A1 | 11/2008 | Lessnick |
| 2008/0312199 A1 | 12/2008 | Glinsky |
| 2009/0011709 A1 | 1/2009 | Akasaka et al. |
| 2009/0017080 A1 | 1/2009 | Tanner et al. |
| 2009/0036415 A1 | 2/2009 | Rubin et al. |
| 2009/0064349 A1 | 3/2009 | Goldstein et al. |
| 2009/0098538 A1 | 4/2009 | Glinsky |
| 2009/0170715 A1 | 7/2009 | Glinsky |
| 2009/0186951 A1 | 7/2009 | Brody et al. |
| 2009/0220488 A1 | 9/2009 | Gardner |
| 2009/0298113 A1 | 12/2009 | Vielhaber et al. |
| 2010/0047361 A1 | 2/2010 | Perrier et al. |
| 2010/0093611 A1 | 4/2010 | Horrigan et al. |
| 2010/0113585 A1 | 5/2010 | Falkowski |
| 2010/0189669 A1 | 7/2010 | Hakozaki |
| 2010/0203043 A1 | 8/2010 | Ree et al. |
| 2010/0256001 A1 | 10/2010 | Niculescu |
| 2010/0273676 A1 | 10/2010 | Naar et al. |
| 2010/0285001 A1 | 11/2010 | Land et al. |
| 2010/0292085 A1 | 11/2010 | Lum et al. |
| 2010/0298329 A1 | 11/2010 | Shaw et al. |
| 2011/0010100 A1 | 1/2011 | Li et al. |
| 2011/0015869 A1 | 1/2011 | Watters et al. |
| 2011/0045998 A1 | 2/2011 | Niculescu et al. |
| 2011/0092695 A1 | 4/2011 | Chen et al. |
| 2011/0098188 A1 | 4/2011 | Niculescu et al. |
| 2011/0150775 A1 | 6/2011 | Slonim et al. |
| 2011/0150798 A1 | 6/2011 | Bacus |
| 2011/0160080 A1 | 6/2011 | Chang |
| 2011/0217701 A1 | 9/2011 | Carter et al. |
| 2011/0251087 A1 | 10/2011 | Glinsky |
| 2011/0263693 A1 | 10/2011 | Vinson-Hieronymus et al. |
| 2011/0269852 A1 | 11/2011 | McDaniel |
| 2012/0116081 A1 | 5/2012 | Shieh et al. |
| 2012/0149773 A1 | 6/2012 | Park et al. |
| 2012/0258074 A1 | 10/2012 | Mills et al. |
| 2012/0283112 A1 | 11/2012 | Binder |
| 2013/0165470 A1 | 6/2013 | Isfort et al. |
| 2013/0170739 A1 | 7/2013 | Hosoi |
| 2013/0189381 A1 | 7/2013 | Dal Farra et al. |
| 2013/0203712 A1 | 8/2013 | Adams et al. |
| 2013/0217589 A1 | 8/2013 | Xu |
| 2013/0259816 A1 | 10/2013 | Hakozaki |
| 2013/0261006 A1 | 10/2013 | Hakozaki |
| 2013/0261007 A1 | 10/2013 | Hakozaki |
| 2013/0261024 A1 | 10/2013 | Hakozaki |
| 2013/0309217 A1 | 11/2013 | Schmidt |
| 2013/0331342 A1 | 12/2013 | Youngquist et al. |
| 2013/0337087 A1 | 12/2013 | Finlay et al. |
| 2015/0125559 A1 | 5/2015 | Osorio |
| 2015/0232945 A1 | 8/2015 | Brody et al. |
| 2015/0292018 A1 | 10/2015 | Binder et al. |
| 2017/0140097 A1 | 5/2017 | Xu et al. |

FOREIGN PATENT DOCUMENTS

| | | |
|---|---|---|
| FR | 2925331 | 4/2010 |
| GB | 849433 A1 | 9/1960 |
| JP | 2008245558 A | 10/2008 |
| JP | 2010099015 A | 5/2010 |
| JP | 2010172240 A | 8/2010 |
| JP | 5234666 B2 | 7/2013 |
| JP | 2014502843 | 2/2014 |
| JP | 5513028 B2 | 6/2014 |
| JP | 5522717 B2 | 6/2014 |
| KP | 2013058107 | 6/2013 |
| KP | 20130125969 | 11/2014 |
| WO | WO0191700 A2 | 12/2001 |
| WO | WO 2003/100557 A2 | 12/2003 |
| WO | WO2004080380 A2 | 9/2004 |
| WO | WO2007077257 A2 | 7/2007 |
| WO | WO2007111899 A2 | 10/2007 |
| WO | WO2007114896 A2 | 10/2007 |
| WO | WO2007117466 A2 | 10/2007 |
| WO | WO2008021483 A2 | 2/2008 |
| WO | WO2008086182 A2 | 7/2008 |
| WO | WO2008086452 A2 | 7/2008 |
| WO | WO2008124428 A1 | 10/2008 |
| WO | WO2009102957 A2 | 8/2009 |
| WO | WO 2009/135915 A1 | 11/2009 |
| WO | WO2009155009 A1 | 12/2009 |
| WO | WO2010060055 A1 | 5/2010 |
| WO | WO2010062372 A2 | 6/2010 |
| WO | WO2010068794 A2 | 6/2010 |
| WO | WO2010093564 A1 | 8/2010 |
| WO | WO 2011/007337 A2 | 1/2011 |
| WO | WO2011028819 A1 | 3/2011 |
| WO | WO2011041912 A1 | 4/2011 |
| WO | WO2011041914 A1 | 4/2011 |
| WO | WO2011075032 A1 | 6/2011 |
| WO | WO2011103449 A2 | 8/2011 |
| WO | WO2011127150 A2 | 10/2011 |
| WO | WO2011133538 A1 | 10/2011 |
| WO | WO 2014/028572 A3 | 2/2014 |
| WO | WO2014028568 | 2/2014 |
| WO | WO2014028569 A2 | 2/2014 |

OTHER PUBLICATIONS

Y. Ishimatsu-Tsuji et al: "Identification 7-15 of novel hair-growth inducers by means of connectivity mapping". The FASEB Journal, vol. 24, No. 5, May 1, 2010.

Mills, K. "Transcriptomic 1-15 Profiling Reveals New Insights Into the Pathogenesis of Dandruff / Seborrheic Dermatitis and the Efficacy of ZPT", 22nd world congress of dermatology. May 24, 2011.

P. Nenoff et al: "The Antifungal Activity of a coal tar gel on Malassezia furfur in vitro" Dermatology 1994; 191(4):311-4.

Luciana Lorena Molinero et al: 1-15 "Up-regulated expression of MICA and proinflammatory cytokines in skin biopsies from patients with seborrhoeic dermatitis". Clinical Immunology, vol. 106, No. 1, Jan. 1, 2003.

Annika M. Saaf et al: "Global Expression Profiling in Atopic Eczema Reveals Reciprocal Expression of Inflammatory and Lipid Genes". PLOS ONE. vol. 3. No. 12, Jan. 1, 2008.

"22nd World Congress of Dermatology", May 24, 2011 (May 24, 2011), from the Internet: URL:http://www.pgbeautygroomingscience.com/ assets/ files/ WCD2011briefingbookno posters_small.pdf.

Lamb, et al. Gene Set Enrichment Analysis (GSEA) (2005) Proc. Natl.Acad Sci U.S.A, 102, 15545-15550.

IPRP PCT/US2012/031509; International filing date Mar. 30, 2012; 11 pages.

(56) References Cited

OTHER PUBLICATIONS

Aden et al, "Proteomic analysis of scleroderma lesional skin reveals activated wound healing phenotype of epidermal cell layer," Rheumatology 2008; 47: 1754-1760.

Blumenberg, "DNA Microarrays in Dermatology and Skin Biology," OMICS: A Journal of Integrative Biology, Oct. 2006, 10(3): Abstract.

Golub et al, "Molecular classification of cancer: class discovery and class prediction by gene expression monitoring," Science, Oct. 15, 1999; 286 (5439): 531-7.

Ishimatsu-Tsuji et al, "Idnetification of novel hair-growth inducers by means of connectivity mapping," The Faseb Journal, 24, 1789-1496 (2010).

Lamb et al, "The Connectivity Map: Using Gene-Expression Signatures to Connect Small Molecules, Genes, and Disease," Science, vol. 313 Sep. 29, 2006.

Lamore et al, "The topical antimicrobial zinc pyrithione is a heat shock response inducer that causes DNA damage and PARP-dependent energy crisis in human skin cells," Cell Stress and Chaperones (2010) 15:309-322.

Niacinamide Research Update, P&G Beauty, 2011, pp. 1-6.

Palchaudhuri et al, "Transcript Profiling and RNA Interference as Tools to Identify Small Molecule Mechanisms and Therapeutic Potential," ACS Chem Biol. Jan. 21, 2011; 6(1): 21-33.

Office Actions for U.S. Appl. No. 13/911,698; P&G Case 12310M; Youngquist et al; filed Jun. 6, 2013.

Office Actions for U.S. Appl. No. 13/402,102; P&G Case 12002M; Binder et al; filed Feb. 22, 2012.

Office Actions for U.S. Appl. No. 14/749,717; P&G Case 12002MD; Binder et al; filed Jun. 25, 2015.

Office Actions for U.S. Appl. No. 14/749,779; P&G Case 12002MD2; Binder et al; filed Jun. 25, 2015.

Office Actions for U.S. Appl. No. 13/851,858; P&G case 12359M; Hakozaki et al; filed Mar. 27, 2013.

Office Actions for U.S. Appl. No. 13/851,873; P&G case 12359M3; Hakozaki et al; filed Mar. 27, 2013.

Office Actions for U.S. Appl. No. 13/851,864; P&G case 12359M2; Hakozaki et al; filed Mar. 27, 2013.

Office Actions for U.S. Appl. No. 13/851,886; P&G case 12359M4; Hakozaki et al; filed Mar. 27, 2013.

Till et al., Characterization of AKT Independent Effects of the Synthetic AKT Inhibitors SH-5 and SH-6 Using an Integrated Approach Combining Transcriptomic Profiling and Signaling Pathway Perturbations, BMC Cancer 2010, 10:287, http://www.biomedcentral.com/1471-2407-10-287.

"Genomics of Skin Aging: Practical Applications", Journal of Drugs in Dermatology Supplement, vol. 8, issue 7 (2009).

"In Vitro Biomarker Responses to a New Anti-Aging Peptide", PAL-KT, Osborne et al., American Academy of Dermatology 67th Annual Meeting Media Resources, 2009.

Affymetrix HGU 133A 2.0 (Release 33, submitted Oct. 30, 2012), Affymetrix.com.

Anti-Age Care Eye Contour Record ID: 806021; Orlane Hypnotherapy; Nov. 2007; Mintel www.gnpd.com.

Aoki et al. British Journal of Dermatology 156.6 (2007): 1214-1223.

Arsic, I., et al. "Preparation of Novel Apigenin-Enriched, Liposomal and Non-Liposomal, Antiinflammatory Topical Formulations as Substitutes for Corticosteroid Therapy" Phytotherapy Research, 25: 228-233 (2011) 6 pages.

Bhogal et al., Toxicity Testing: creating a revolution based on new technologies, TRENDS in Biotechnology, vol. 23, No. 6, Jun. 2005, pp. 299-307.

Bier et al., "DNA Microarrays" Adv. Biochem. Eng. Biotechnol., 109:433-53 (2008).

Boyle, Jay et al., "Effects of Cigarette Smoke on the Human Oral Mucosal Transcriptome", Cancer Prev Res, Mar. 2010; 3(3): 266-278.

Chang, Meiping et al., "Evaluation of Phenoxybenzamine in the CFA Model of Pain Following Gene Expression Studies and Connectivity Mapping", Molecular Pain 2010, 6:56, http://www.molecularpain.com/content/6/1/56.

Choi, H., et al., "Labisia Pumila Extract Protects Skin Cells From Photoaging Caused by UVB Irradiation" Journal of Bioscience and Bioengineering, vol. 109, No. 3, 2010, 6 pages.

Coombs, GS., et al., Modulation of Wnt/B-Catenin Signaling nad Proliferation by a Ferrous Iron Chelator With Therapeutic Efficacy in Genetically Engineered Mouse Models of Cancer, Oncogene (2012) 31, 213-225 & 2012 Macmillan Publishers Limited.

Cork et al., "Epidermal barrier dysfunction in atopic dermatitis" J. Invest Dermatol., 129(8); 1892-908 (2009).

Cui et al., "Statistical Tests for Differential Expression in cDNA Microarray Experiments", Genome Biology, Biomed Central LTD, GB, vol. 4, pp. 210-219, Mar. 17, 2003.

Dark Circle Eye Treatment Record ID: 1126479; Manceuticals; Aug. 2008; Mintel www.gnpd.com.

de Magalhães, Ageing research in the post-genome era: New technologies for an old problem, pp. 99-115 in Redox Metabolism and Longevity Relationships in Animals and Plants, vol. 62, Feb. 2009.

Ding-Dar, L. "Retinoid-Responsive Transcriptional Changes in Epidermal Keratinocytes" J. Cellular Physiology 220: pp. 427-329; 2009.

Draelos "Clinical Situations Conducive to Proactive Skin Health and Anti-Aging Improvement", The Society for Investigative Dermatology 2008, pp. 25-27.

Eye Anti-Aging Moisturizing Treatment Record ID: 600664; Elizabeth Arden; Oct. 2006; Mintel www.gnpd.com.

Eye Express Radiance Ice Cubes Record ID: 1295582; Anne Semonin; Mar. 2010; Mintel www.gnpd.com.

Fan et al., "Illumina universal bead arrays" Methods Enzymol., 410:57-73 (2006).

Fisher, G.J., "Pathophysiology of Premature Skin Aging Induced by Ultraviolet Light" The New England Journal of Medicine; vol. 337, No. 20, Nov. 13, 1997, 10 pages.

Fujita, "Multivariate gene expression analysis reveals functional connectivity changes between normal/tumoral prostates", BMC Systems Biology, vol. 2, issue 106, 14 pages, Dec. 2008.

Gheeya, J., et al., Expression Profiling Identifies Epoxy Anthraquinone Derivative as a DNA Topoisomerase Inhibitor, Cancer Ltt. Jul. 2010 1:293(1): 124-31.

Gilcrest, B.A., "Ageing and Photoageing of the Skin: Observations at the Cellular and Molecular Level" British Journal of Dermatology (1992) 127, Supplement 41, 6 pages.

Guttman-Yassky E., et al., "Major differences in inflammatory dendritic cells and their products distinguish atopic dermatitis from psoriasis", J. Allergy Clin. Immunol., vol. 119, No. 5, pp. 1210-1217, May 2007, USA.

Hakozaki et al. (2002) British Journal of Dermatology 147.1 (2002): 20-31.

Hassan, S.B., et al., Alpha Terpineol: A Potential Anticancer Agent Which Acts Through Suppression NF-Kappab Signaling, Anticancer Res. Jun. 2010;30(6): 1911-9.

Hassane, D.C., et al., Chemical Genomic Screening Reveals Synergism Between Parthenolide and Inhibitors of the PI-3 Kinase and Mtor Pathways, Blood. Dec. 23, 2010; 116(26)5983-90.

Hegyi, A., et al. Vitamin D Analog Calcipotriol Suppresses the Th17 Cytokine-Induced Proinflammatory S100 "Alarmins" Psoriasin (S100A7) and Koebnerisin "S100A15 in Psoriasis" Journal of Investigative Dermatology 2012, vol. 132, 9 pages.

Hoheisel, "Microarray Technology: Beyond Transcript Profiling and Genotype Analysis" Nat. Rev. Genet., 7:200-10 (2006).

Hollander, M., et al., "Nonparametric Statistical Methods", Wiley, New York, ed. 2, 1999, pp. 178-185.

Hong, Y. et al., A 'Metastassis-Prone' Signature for Early-Stage-Mismatch-Repair Proficient Sporadic Colorectal Cancer Patients and Its Implications for Possible, Therapeutics. Clin Exp Metastasis, Feb. 2010; 27(2):83-90.

Hughes, T.R., et al. "Functional discovery via a compendium of expression profiles" Cell vol. 102, 109-126 (2000).

Iskar, M. et al., "Drug-Induced Regulation of Target Expression," PLoS Computational, Sep. 2010, vol. 6, Issue 9, e1000925.

(56) References Cited

OTHER PUBLICATIONS

Jagetia G.C., et al., "Genotoxic Effect of Hydroquinone on the Cultured Mouse Spleenocytes" Toxicology Letter 121(1); 15-20, 2001.

Jensen et al., "Acid and neutral sphingomyelinase, cermide synthase, and acid ceramidase activities in cutaneous aging" Experimental Dermatology 2005, p. 609-616.

Johnson et al., "Adjusting Batch Effects in Microarray Expression Data Using Empirical Bayes Methods", Biostatistics, vol. 8, No. 1, pp. 118-127, Jan. 1, 2007.

Johnson, "Skin conditions and related need for medical care amount persons 1-74 years, United States, 1971-1974", Vital and Health Statistics Series 11, No. 212, DHEW publication No. (PHS) 79/1660, U.S. Department of Health, Education and Welfare, National Center for Health Statistics 1978: 1-72.

Josset<Laurence et al. "Gene Expression Signature-Based Screening Identifies New Broadly Effective Influenza A Antivirals," PLoS ONE, www.plosone.org, Oct. 2010, vol. 5, issue 10, e13169.

Kang et al. (Journal of Investigative Dermatology (2011) 131, 1692-1700.

Kimata et al., "Enhancement of Allergic Skin Wheal Responses by Microwave Radiation from Mobile Phones in Patients with Atopic Eczema/Dermatitis Syndrome" Int Arch of Allergy and Immunology, 129 (4): 348-350 (2002).

Kluken et al., "Atopic eczema/dermatitis syndrome—a genetically complex disease. New advances in discovering the genetic contribution" Allergy, 58(1):5-12 (2003).

Kunkel, Steven D., "mRNA Expression Signatures of Human Skeletal Muscle Atrophy Identify a Natural Compound That Increases Muscle Mass", Cell Metab. Jun. 8, 2011; 13(6): 627-638.

Lachmann, Alexander et al., ChEA: Transcription Factor Regulation Inferred from Integrating Genome-Wide Chip-X Experiments, vol. 26, No. 19, 2010, pp. 2438-2444.

Lei Huang et al., An Integrated Bioinformatics Approach Identifies Elevated Cyclin E2 Expression and E2F Activitiy as Distinct Features of Tamoxifen Resistant Breast Tumors, Plos One, Jul. 1, 2011, vol. 6, issue 7, e22274.

Mcart, Darragh G., et al., Identification of Candidate Small-Molecule Therapeutics to Cancer by Gene-Signature Perturbation in Connectivity Mapping, PLos ONE, www.plosone.org., Jan. 2011, vol. 6, issue 1.

Mihaly, J., "Decreased retinoid concentration and retinoid signaling pathways in human atopic dermatitis" 2011 John Wiley & Sons, Experimental Dermatology, 20, pp. 326-330.

Millikin, Cheri et al. "Topical N-acetyl glucosamine and niacinamide affect pigmentation relevant gene expression in in vitro geonomics experimentation" Journal American Academy of Dermatology, Feb. 2007.

Mobini, R., et al. "A module-based analytical strategy to identity novel disease-associated genes shows an inhibitory role for interleukin 7 Receptor in allergic inflammation", BMC Syst Biol; 3:19 (2009).

Mockler et al., "Applications of DNA tiling arrays for whole-genome analysis" Genemics, 85:1-15(2005).

Muller, Klaus Robert et al., "An Introduction to Kernel Based Learning Algorithms", IEEE Transactions on Neural Networks, vol. 12 No. 2, Mar. 2001.

Nair et al., "Genome-wide scan reveals association of psoriasis with IL-23 and NF-kappaB pathways", Nat Genet; 41(2): 199-204 (2009).

Olsson, M. et al. "Increased expression of aquaporin 3 in atopic eczema", Allergy; 61(9); 1132-7.

PCT International Search Report and Written Opinion for PCT US2013/034055 dated Jun. 11, 2013.

PCT International Search Report and Written Opinion for PCT/ US2012/026145 dated Jan. 22, 2014.

PCT International Search Report and Written Opinion for PCT/ US2013/034052 dated Mar. 27, 2013.

PCT International Search Report and Written Opinion for PCT/ US2013/034054 dated Jun. 13, 2013.

PCT International Search Report and Written Opinion for PCT/ US2013/034117 dated Jun. 11, 2013.

PCT International Search Report and Written Opinion for PCT/ US2013/054855 dated Oct. 30, 2013.

PCT International Search Report and Written Opinion for PCT/ US2013/054857 dated Oct. 28, 2013.

PCT International Search Report and Written Opinion for PCT/ US2013/054861 dated Apr. 4, 2014.

PCT International Search Report and Written Opinion for PCT/ US2013/055138 dated Nov. 12, 2013.

PCT International Search Report dated Jul. 9, 2013—6 pages.

PCT Invitation to Pay Additional Fees for PCT/US2012/026145 dated Apr. 5, 2013.

Pels, et al. "Clobetasol Propionate—Where, When, Why?", Drugs of Today 2008, 44(7); 547-557.

Plager, D. et al. "Early Cutaneous gene transcription changes in adult atopic dermatitis and potential clinical implications", Exp Dermatol; 16(1):28-36 (2007).

Ranu et al. "Periorbital Hyperpigmentation in Asians: An Epidemiologic Study and a Proposed Classification"Dermatol Surg 2011;37:1297-1303 (2011).

Raqoussis & Elvidger, "Affymetrix GeneChip system; moving from research to the Clinic" Expert Rev. Mo. Diagn., 6:145-52 (2006).

Raynaud, E., et al., "Depigmentation for cosmetic purposes: prevalence and side-effects in a female population in Senegal"Ann Dermatol Venereol 128 (6-7): 720-724, 2001 (abstract).

Renshaw, Derek et al., Downstream Gene Activation of the Receptor ALX by the Agonist Annexin A1, LoS One, www.plosone.org, Sep. 2010, vol. 5, issue 9.

Rho, SB et al., "A Gene Signature-Based Approach Identifies Thioridazine as an Inhibitor of Phosphatidylinosito1-3'Kinase (PI3K)/ AKT Pathway in ovarian Cancer Cells", Gynecol Oncol. Jan. 2011; 120(1): 121-7.

Robinson et al. (J. Am. Acad. Dermatol. Sup. 60 (2009) [Poster presentation]).

Sanda, Takaomi et al. "Interconnecting Molecular Pathways in The Pathogenesis and Drug Sensitivity of T-Cell Acute Lymphoblastic Leukemia", Blood. Mar. 4, 2010; 115(9): 1735-1745.

Scherf, U., et al., "A gene expression database for the molecular pharmacology of cancer", Nat. Genet. Mar. 2000; 24(3): 236-44.

Sea Buckhom Age Defying Eye Cream Record ID: 1365520; Sibu Beauty; Jul. 2010; Mintel www.gnpd.com.

Shiek SSJ Ahmed et al., "Systems Biological Approach on Neurological disorders: A Novel Molecular Connectivity to Aging and Psychiatric Diseasees", BMC Systems Biology 2011, 5:6 http:// www.biomedcentral.com/1752-0509/5/6.

Shimizu. K, et al., "The skin-lightening effects of artocarpin on UVB-induced pigmention"Planta Med 68(1); 79-81, 2002.

Sivapirabu, G., et al., "Topical Nicotinamide Modulates Cellular Energy Metabolism and Provides Broad-Spectrum Protection Against Ultraviolet Radiation-Induced Immunosuppression in Humans", British Journal of Dermatology 2009.

Skin Biomarkers Confirm the Anti-Oxidant Activity of Olive Derivatives and Yeast Ferment Filtrate, Finlay et al., P&G 67th Annual Meeting of American Academy of Dermatology (2009).

Smalley, JL et al., "Application of Connectivitiy Mapping in Predictive Toxicology Based on Gene-Expression Similarity", Toxicology Feb. 9, 2010; 268(3):143-6.

Smith et al., "The effect of a high-protein, low glycemic-load diet versus a conventional, high glycemic-load diet on biochemical parameters associated with acne vulgaris: A randomized, investigator-masked, controlled trial" Journal of the American Academy of Dermatology, vol. 57 (2); 247-56 (2007).

Stephanopoulos et al., "Mapping Physiological States from Microarray Expression Measurements", Bioinformatics, vol. 18, No. 8, pp. 1054-1063, Aug. 1, 2002.

Subramanian, A. et al., Gene set enrichment analysis: A knowledge-based approach for interpreting genome-wise expression profiles. (2005) Proc. Natl. Acad Sci. U.S.A., 102, 15545-15550.

Swindell et al., "Genome-wide expression profiling of five mouse models identifies similarities and differences with human psoriasis", PLoS One; 6(4); Apr. 2011, 20 pages.

Tjabringa, G. et al. "Development and Validation of Human Psoriatic Skin Equivalents"; The American Journal of Pathology, vol. 173, No. 3, Sep. 2008, 9 pages.

(56) References Cited

OTHER PUBLICATIONS

Trivedi, N. et al. "Gene array expression profiling in acne lesions reveals marked up regulation of genes involved in inflammation and matrix remodeling" J. Invest Dermatol; 126(5); 1071-9 (2006).

Verschoore, et al. "Determination of Melanin and Hemoglobin in the Skin of Idiopathic Cutaneous Hyperchromia of the Orbital Region: A Study of Indian Patients" J Cutan Aesthet Surg. Jul.-Sep. 2012 5(3) 176-182.

Vertuani et al., Determination of antioxidant efficacy of cosmetic formulations by non-invasive measurements, Skin Research and Technology, vol. 9, No. 3, Aug. 2003, pp. 245-253.

Wang et al. "Environmental risk factors for early infantile atopic dermatitis" Pediatr Allergy Immunol., 18(5): 441-7 (2007).

Wang, Guiping et al., Expression-Based in Silico Screening of Candidate Therapeutic Compounds for Living Adenocarcinoma, PLos ONE, www. plosone.org., Jan. 2011, vol. 6, issue 1.

Watson, et al. "A short-term screening protocol, using fibrillin-1 as a reporter molecule, for photoaging repair agents" Journal of Investigative Dermatology, vol. 116, No. 5, May 2001 (May 2001), pp. 672-678.

Wen, Zhining et al., "Discovery of Molecular Mechanisms of Traditional Chinese Medicinal Formula Si-Wu-Tang Using Gene Expression Microarray and Connectivity Map", PLoS ONE, www.plosone.org, Mar. 2011, vol. 6, issue 3, e18278.

Westra< Jurjen et al., "Construction of a Computable Cell Proliferation Network Focused on Non-Diseased Lung Cells," BMC Systems Biologoy 2011, 5:105, http://www.biomedcentral.com/1752-0509-5/105.

Wood, TE et al., "Selective Inhibition of Histone Deacetylases Sensitizes Malignant Cells to Death Receptor Ligands, 1", Mol. Cancer Ther. Jan. 2010; 9(1):246-56; Epub Jan. 6, 2010.

Yumiko, I., et al., "Identification o Novel Hair-Growth Inducers by means of Connectivity Mapping", FASEB Journal, vol. 24, May 2010.

Zhang, Z., et al. "A Novel Compound From a Combinatorial Library, Arrests Mitosis via Inhibiting The Polymerization of Microtubules", Invest New Drugs, Dec. 2010; 28(6):715-28.

Zimmer, Michael et al., "The Connectivity Map links Iron Response Protei-1 (IRP!)-medicated inhibition of HIF2a translation to the anti-inflammatory 15-deoxy-12, 14-Prostaglandin J2," Cancer Res. Apr. 15, 2010; 70(8); 3071-3079.

Zouboulis, C.C., et al. "Clinical Aspects and Molecular Diagnostics of Skin Aging" Clinics in Dermatology (2011) 29, 12 pages.

Bissett, Donald, et al., "Genomic Expression Changes Induced by Topical N-Acetyl Glucosamine in Skin Equivalent Cultures in Vitro" Journal of Cosmetic Dermatology, Feb. 2007.

| Table A | | | Table B | |
|---|---|---|---|---|
| A | B | C | D | E |
| Lipid immune Signature | | | Dandruff skin signature | |
| Up List | Down List | | Up List | Down List |
| 209470_at | 201275_at | | 208276_at | 208525_at |
| 208239_at | 221750_at | | 205916_at | 221249_s_at |
| 220322_at | 201128_s_at | | 211906_s_at | 204872_at |
| 203233_at | 203027_s_at | | 39249_at | 202976_s_at |
| 208774_x_at | 203515_s_at | | 39248_at | 218471_s_at |
| 219403_s_at | 32836_at | | 219630_at | 203697_at |
| 208992_s_at | 202735_at | | 208539_x_at | 209292_at |
| 215223_s_at | 215093_at | | 206332_s_at | 204589_at |
| 207356_at | 209146_at | | 203747_at | 202054_s_at |
| 210367_s_at | 206714_at | | 210138_at | 206149_at |
| 210413_x_at | 208964_s_at | | 201739_at | 218087_s_at |
| 216388_s_at | 204615_x_at | | 201644_at | 217781_s_at |
| 202411_at | 202218_s_at | | 36936_at | 221527_s_at |
| 205863_at | 200862_at | | 203535_at | 218820_at |
| 202687_s_at | 210130_s_at | | 210413_x_at | 218528_s_at |
| 216598_s_at | 204515_at | | 213857_s_at | 218142_s_at |
| 202018_s_at | 202539_s_at | | 206628_at | 205807_s_at |
| 222223_s_at | 36907_at | | 220658_s_at | 203698_s_at |
| 203005_at | 212218_s_at | | 211075_s_at | 221834_at |
| 203882_at | 210950_s_at | | 205595_at | 213348_at |
| 208650_s_at | 202321_at | | 209720_s_at | 201117_s_at |
| 208762_s_at | 218922_s_at | | 209124_at | 204363_at |
| 203536_at | 201791_s_at | | 208865_at | 204032_at |
| 209732_at | 220081_x_at | | 209719_x_at | 213227_at |
| 202357_s_at | 205709_at | | 205436_s_at | 211941_s_at |
| 209124_at | 218434_s_at | | 207168_s_at | 222362_at |
| 202917_s_at | 219632_at | | 200660_at | 221476_s_at |
| 206332_s_at | 220675_s_at | | 219403_s_at | 209291_at |
| 212067_s_at | 211423_s_at | | 221698_s_at | 212071_s_at |
| 219095_at | 214584_x_at | | 202917_s_at | 208407_s_at |
| 204420_at | 204607_at | | 220966_x_at | 218655_at |
| 202869_x_at | 216715_s_at | | 217755_at | 219132_at |
| 212581_at | 202314_at | | 204300_at | 212321_at |

FIG. 1A

|    |             |            |   |             |             |
|----|-------------|------------|---|-------------|-------------|
| 36 | 218400_at   | 216080_s_at|   | 33323_r_at  | 210987_x_at |
| 37 | 208607_s_at | 57163_at   |   | 205159_at   | 203766_s_at |
| 38 | 210797_s_at | 204476_s_at|   | 205847_at   | 203296_s_at |
| 39 | 202948_at   | 219735_s_at|   | 206004_at   | 212510_at   |
| 40 | 208771_s_at | 201339_s_at|   | 220664_at   | 221748_s_at |
| 41 | 205159_at   | 218869_at  |   | 200734_s_at | 215945_s_at |
| 42 | 212203_x_at | 209577_at  |   | 210367_s_at | 217906_at   |
| 43 | 201096_at   | 203217_s_at|   | 209800_at   | 203081_at   |
| 44 | 201422_at   | 212329_at  |   | 204715_at   | 215235_at   |
| 45 | 212659_s_at | 32837_at   |   | 208436_s_at | 218625_at   |
| 46 | 203964_at   |            |   | 217834_s_at | 221747_at   |
| 47 | 200923_at   |            |   | 209260_at   | 209108_at   |
| 48 | 202086_at   |            |   | 222062_at   | 201701_s_at |
| 49 | 208829_at   |            |   | 206337_at   | 205412_at   |
| 50 | 204972_at   |            |   | 204858_s_at | 203824_at   |
| 51 | 210784_x_at |            |   | 206661_s_at | 207961_x_at |
| 52 | 202257_s_at |            |   | 201594_s_at | 213182_x_at |
| 53 | 204415_at   |            |   | 214226_at   | 201989_s_at |
| 54 | 204103_at   |            |   | 208850_s_at | 212372_at   |
| 55 | 200905_x_at |            |   | 209191_at   | 201497_x_at |
| 56 | 202953_at   |            |   | 208696_at   | 219440_at   |
| 57 | 215990_s_at |            |   | 201422_at   | 202255_s_at |
| 58 | 207277_at   |            |   | 219956_at   | 202747_s_at |
| 59 | 201786_s_at |            |   | 213923_at   | 207233_s_at |
| 60 | 203717_at   |            |   | 219099_at   | 217897_at   |
| 61 | 216834_at   |            |   | 208540_x_at | 202724_s_at |
| 62 | 201926_s_at |            |   | 218960_at   | 219304_s_at |
| 63 | 209189_at   |            |   | 208851_s_at | 204712_at   |
| 64 |             |            |   | 209825_s_at | 208820_at   |
| 65 |             |            |   | 211762_s_at | 209733_at   |
| 66 |             |            |   | 214580_x_at | 206015_s_at |
| 67 |             |            |   | 201890_at   | 213900_at   |
| 68 |             |            |   | 220322_at   | 203498_at   |
| 69 |             |            |   | 203233_at   | 209071_s_at |
| 70 |             |            |   | 203256_at   | 213050_at   |
| 71 |             |            |   | 218335_x_at | 221958_s_at |
| 72 |             |            |   | 217028_at   | 218418_s_at |

FIG. 1B

| PHYSIOLOGICAL PROCESS | DANDRUFF INVOLVED VS. UNINVOLVED | DANDRUFF INVOLVED VS. NON-DANDRUFF | DANDRUFF UNINVOLVED VS. NON-DANDRUFF |
|---|---|---|---|
| LIPID METABOLISM | ↓ | ↓ | ↓ |
| IMMUNE RESPONSE | ↑ | ↑ | ↑ |
| CELL PROLIFERATION | ↑ | ↑ | ↓ |
| APOPTOSIS | ↓ | ↓ | ↓ |
| CELL DIFFERENTIATION | ↓ | ↓ | ↓ |

FIG. 9

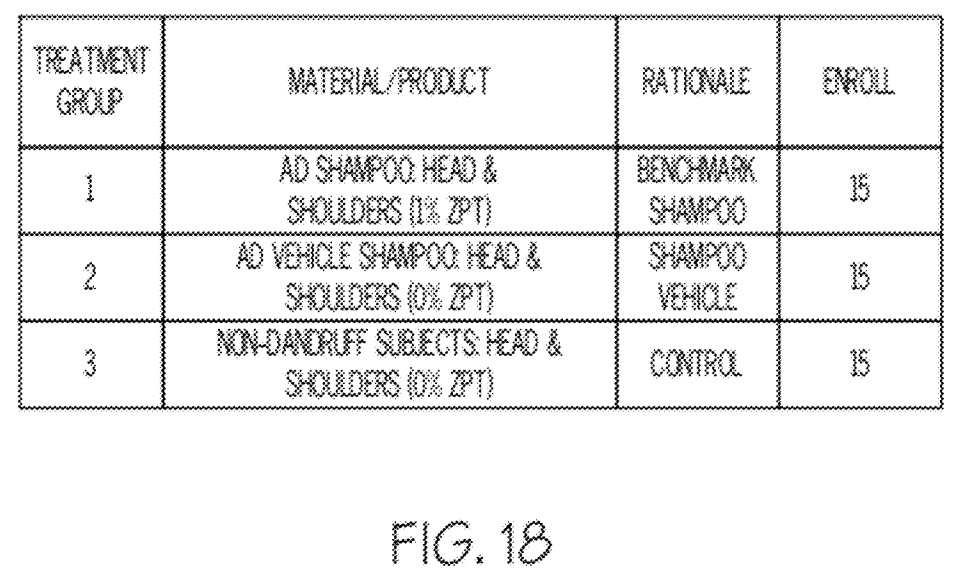

| TREATMENT GROUP | MATERIAL/PRODUCT | RATIONALE | ENROLL |
|---|---|---|---|
| 1 | AD SHAMPOO HEAD & SHOULDERS (1% ZPT) | BENCHMARK SHAMPOO | 15 |
| 2 | AD VEHICLE SHAMPOO HEAD & SHOULDERS (0% ZPT) | SHAMPOO VEHICLE | 15 |
| 3 | NON-DANDRUFF SUBJECTS HEAD & SHOULDERS (0% ZPT) | CONTROL | 15 |

FIG. 18

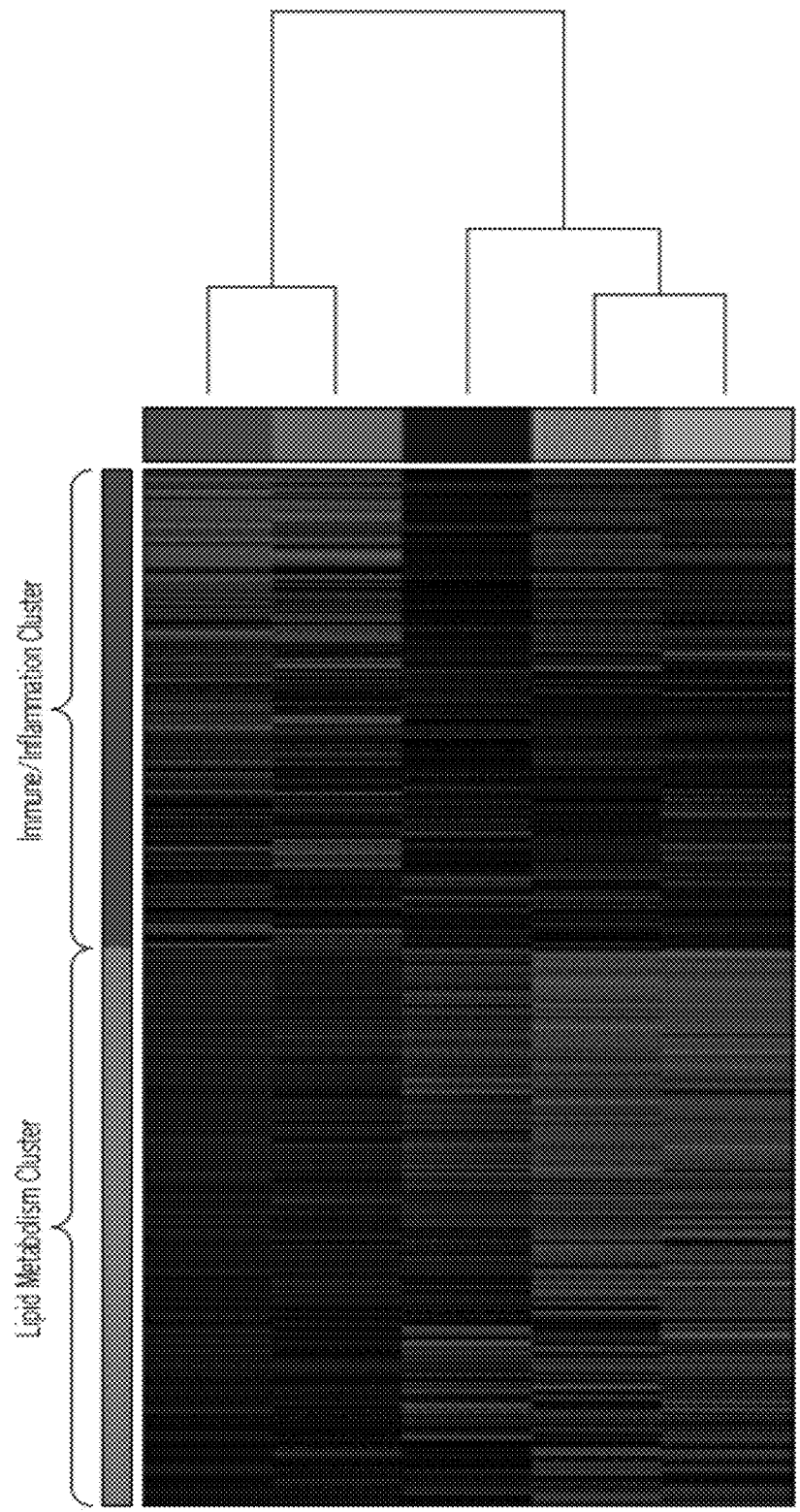

| Biological Processes in GO | Dandruff | IL17 + IL22 | IL1β | IL17 | IL22 | IL24 | IFNγ | Clobet asol Propio nate | Climb azole | Keto cona zole | SeS | ZPT |
|---|---|---|---|---|---|---|---|---|---|---|---|---|
| Epithelial cell differentiation (Keratinocyte differentiation) | Up | Up-wk | No | No | No | No | No | No | No | No | No | No |
| M phase of mitotic cell cycle | No | No | No | No | No | No | No | Dn | Dn-wk | Dn | No | No |
| nuclear division | No | No | No | No | No | No | No | Dn | Dn-wk | Dn | No | No |
| cellular response to DNA damage stimulus | No | No | No | No | No | No | No | Dn | No | Dn | No | No |
| DNA metabolic process | No | No | No | No | No | No | No | Dn | No | Dn | No | No |
| Positive regulation of programmed cell death | No | No | No | No | No | No | Up-wk | No | No | No | No | No |
| Negative regulation of programmed cell death (Anti-apoptosis) | Up - wk | Up-wk | Up | No | No | No | Up | Up-wk | No | Up-wk | No | No |
| Defense response (inflammatory response) | Up | Up-wk | Up | Up-wk | No | No | Up | No | No | No | No | No |
| Response to wounding | Up | Up | Up | Up-wk | No | No | Up | Up-wk | No | No | No | No |
| Response to biotic stimulus | Up | Up | Up | No | No | No | Up | No | No | Dn-wk | No | No |
| Response to hormone stimulus | Up - wk | Up | No | No | No | No | Up-wk | Up | No | Up-wk | No | No |
| Antigen processing and presentation | Up | No | No | No | No | No | Up | No | No | No | No | No |
| leukocyte mediated immunity | Up | No | No | No | No | No | Up | No | No | No | No | No |

FIG. 21A

| Biological Processes in GO | Dandruff | IL17 + IL22 | IL1β | IL17 | IL22 | IL24 | IFNγ | Clobet asol Propionate | Climb azole | Keto cona zole | SsS | ZPT |
|---|---|---|---|---|---|---|---|---|---|---|---|---|
| Cellular ketone metabolic process | Dn | Dn | No | No | No | No | No | No | No | Up | No | No |
| Lipid metabolic process (lipid biosynthetic process) | Dn | Dn | Dn-very wk | Up-wk | No | No | No | Up-wk | Up-wk | Up | No | No |
| Steroid metabolic process (Steroid biosynthetic process) | Dn | No | No | No | No | No | No | Up | Up | Up | No | No |

FIG. 21B

SYSTEMS, MODELS AND METHODS FOR IDENTIFYING AND EVALUATING SKIN-ACTIVE AGENTS EFFECTIVE FOR TREATING DANDRUFF/SEBORRHEIC DERMATITIS

PRIORITY

This application claims priority under 35 U.S.C. § 119(e) to U.S. Provisional Applications 61/470,131 filed on Mar. 31, 2011, 61/488,501 filed on May 20, 2011, and 61/519,504, filed on May 24, 2011, the entire disclosures of which are incorporated herein by this reference.

BACKGROUND OF THE INVENTION

Dandruff, alternatively referred to in the literature as ptyriasis simplex, furfuracea or capitis, is a skin disorder characterized by flaking, itching and microinflammation. By definition, dandruff is confined to the scalp, and it is experienced by about half of the adult population irrespective of ethnicity and gender. Dandruff has conventionally been considered trivial from a medical standpoint, but represents a persistent cosmetic concern.

Dandruff is considered to be a form of seborrheic dermatitis, which may be found in other locations on the body. Scalp scaling, which is present in both disorders, is not the clinical distinguishing feature. Rather, inflammation and presence of lesions outside the scalp exclude the diagnosis of dandruff. Generally, dandruff is considered the mildest form of seborrheic dermatitis from a clinical perspective since inflammation is minimal and typically subclinical. In fact, as recently as a decade ago the dandruff condition was thought to be non-inflammatory. The term "dandruff" is also used to describe the symptomatic scale itself, which has conventionally been considered as subject to cosmetic management. Response to currently available cosmetic treatments, however, is often transient. In contrast, seborrheic dermatitis is a more inflammatory disease and medical treatment is often undertaken to clear the disease, although cosmetics may also demonstrate some efficacy in reducing symptoms.

Dandruff scale comprises a cluster of corneocytes which have retained a large degree of cohesion with one another and which become detached as such from the surface of the stratum corneum. The size and degree of scaling is inconsistent across the region of the scalp and as a function of time. One hypothesis of dandruff formation relates to a suppression of the lipases responsible for proper shedding of corneocytes at the skin surface.

The pathogenesis of dandruff is complex, and appears to be the result of interactions between scalp skin, cutaneous microflora and the cutaneous immune system. The key clinical features of dandruff include flaking and itch, and although much descriptive work has been done, the precise underlying events that provoke these symptoms are incompletely understood. Dandruff is considered to have multiple sometimes overlapping causes with numerous pathogenic pathways and complex mechanisms. A microbial flora is implicated in the most common forms of dandruff. Generally, a healthy normal scalp is known to harbor many microbes reaching a density of $10^3$ to $10^5$ organisms per $mm^2$ and including, for example, *Staphylococci, Propionibacterium* spp. and *Malassezia* spp.

The theory that dandruff is fundamentally a *Malassezia*-based disorder remains prevalent. However, as the clinical evidence implicating *Malassezia* in dandruff conditions and seborrheic dermatitis has accumulated over time, it has been observed that results obtained from quantitative methods used to count yeasts are inconsistent and do not correlate. For example, no relationship has been found between severity of symptoms and fungal count. It is hypothesized that only yeasts that are tightly bound to the skin correlate to the dandruff condition. Further perplexing however is that quantitative microbiological assessments fail to implicate a role specifically for yeast. Some investigators attribute this to a failure to note the relationship between dandruff and particular species of *Malassezia*. Regardless of the inability to account for the inconsistent empirical observations, controlling yeast of the genus *Malassezia* has heretofore been the most successful dandruff management strategy. Application of antifungal-based antidandruff shampoos generally results in lessening or disappearing itch after only a few applications. A problem with this strategy remains in that although anti-fungal management results in a decrease in the yeasts, complete eradication is rarely achieved. Scale production reduces in parallel to microbe reduction, yet within 2 to 3 weeks of ceasing treatment, dandruff recurs and *Malassezia* populations increase to their pre-treatment levels.

Close inspection reveals that the *Malassezia* yeasts appear in scattered clumps restricted in distribution over some corneocytes but not others. It has been hypothesized that dandruff represents a failure of a normal immune response by the specific keratinocytes where *Malassezia* yeasts are found. Other investigators note that *Malassezia* have antigenic and pro-inflammatory properties stimulating both the innate and acquired immune responses. Anti-inflammatory drugs such as dermocorticoids have proven efficacy, particularly in severe dandruff. Nonetheless, providing an antifungal active remains the conventional treatment of choice.

A further confounding problem in determining the causative basis of dandruff is the mode of action of the antifungal agents themselves. Most of the known actives such as zinc pyrithione (ZPT), a biocide widely recognized as an effective anti-fungal agent in shampoo formulations, are substantially insoluble in water so that sustained contact time with the scalp is very brief. Many investigators therefore posit that the anti-fungal agents exhibit efficacy through some ancillary mode of action including some direct biological effects on epidermal cells.

Scaling conditions similar to dandruff may occur with desquamation of the scalp following excessive exposure to sunlight where intercorneocyte cohesion is also affected, as well as in minor chronic irritation of the scalp. Further, over-brushing, over-shampooing, certain cosmetic hair products, and irritation from airborne substances may cause scaling. Other non-fungal causes include use of sebum-derived products, sunlight activation of follicular-photosensitizing agents such as porphyrins, and some neuro-immune conditions. Psychological stress is also widely considered to exacerbate dandruff.

Sebum has been found to be a prerequisite for dandruff, but not a sufficient factor per se. Many people who complain about oily scalp have no dandruff, while successful treatment of dandruff often leads to an increased coating of the hair shafts by sebum. Epidermal lipids exhibit differences across the dandruff condition both in quantity and quality. In particular, it has been demonstrated that the three main classes of stratum corneum lipids, i.e. ceramides, free fatty acids and cholesterol, display diminished content in dandruff-affected relative to healthy scalp skin.

Dandruff severity ranges from mild and discrete to severe and pervasive among affected individuals. Amount of scalp hair is a factor, although amounts of dandruff on the scalp and on hair are not always correlated. Products used to treat dandruff have been observed to suppress androgenic alopecia, and ketoconazole has been reported to stimulate hair growth in mice, among many other effects.

Dandruff, therefore, represents a reactive response of the epidermis of the scalp to various stimuli, some of which may be external and some of which may be internal, in combination with an individual predisposition, and its etiological complexity makes it a treatment challenge. There is a persistent need in the art for methods of identifying potential anti-dandruff agents and for evaluating the efficacy of putative agents having efficacy substantially independent of mechanism of action or etiology of the dandruff condition. The present investigators therefore undertook an investigation into the application of "connectivity mapping" to the search for new skin-active agents with efficacy in the treatment of dandruff and related skin conditions.

Connectivity mapping is a well-known hypothesis generating and testing tool having successful application in the fields of operations research, telecommunications, and more recently in pharmaceutical drug discovery. The undertaking and completion of the Human Genome Project, and the parallel development of very high throughput high-density DNA microarray technologies enabling rapid and simultaneous quantification of cellular mRNA expression levels, resulted in the generation of an enormous amount of gene expression data. At the same time, the search for new pharmaceutical actives via in silico methods such as molecular modeling and docking studies stimulated the generation of vast libraries of potential small molecule actives. The amount of information linking disease to gene expression profiles, gene expression profiles to drugs, and disease to drugs grew exponentially, and application of connectivity mapping as a hypothesis testing tool in the medicinal sciences ripened.

The general notion that functionality could be accurately determined for previously uncharacterized genes, and that potential targets of drug agents could be identified by mapping connections in a data base of gene expression profiles for drug-treated cells, was spearheaded in 2000 with publication of a seminal paper by T. R. Hughes et al. ["Functional discovery via a compendium of expression profiles" *Cell* 102, 109-126 (2000)], followed shortly thereafter with the launch of The Connectivity Map (—map Project by Justin Lamb and researchers at MIT ("Connectivity Map: Gene Expression Signatures to Connect Small Molecules, Genes, and Disease", *Science*, Vol 313, 2006.) In 2006, Lamb's group began publishing a detailed synopsis of the mechanics of C-map construction and installments of the reference collection of gene expression profiles used to create the first generation C-map and the initiation of an on-going large scale community C-map project, which is available under the "supporting materials" hyperlink at http://www.sciencemag.org/content/313/5795/1929/suppl/DC1.

The basic paradigm of predicting novel relationships between disease, disease phenotype, and drugs employed to modify the disease phenotype, by comparison to known relationships has been practiced for centuries as an intuitive science by medical clinicians. Modern connectivity mapping, with its rigorous mathematical underpinnings and aided by modern computational power, has resulted in confirmed medical successes with identification of new agents for the treatment of various diseases including cancer. Nonetheless, certain limiting presumptions challenge application of C-map with respect to diseases of polygenic origin or syndromic conditions characterized by diverse and often apparently unrelated cellular phenotypic manifestations. According to Lamb, the challenge to constructing a useful C-map is in the selection of input reference data which permit generation of clinically salient and useful output upon query. For the drug-related C-map of Lamb, strong associations comprise the reference associations, and strong associations are the desired output identified as hits.

Noting the benefit of high-throughput, high density profiling platforms which permit automated amplification, labeling hybridization and scanning of 96 samples in parallel a day, Lamb nonetheless cautioned: "[e]ven this much firepower is insufficient to enable the analysis of every one of the estimated 200 different cell types exposed to every known perturbagen at every possible concentration for every possible duration . . . compromises are therefore required," Lamb, J. (2007) "The Connectivity Map: a new tool for biomedical research" Nat. Rev. Cancer 7, 54-60, (page 54, column 3, last paragraph). Lamb, however, took the position that cell type did not ultimately matter, and confined his C-map to data from a very small number of established cell lines out of efficiency and standardization concerns. Theoretically this leads to heightened potential for in vitro to in vivo mismatch, and limits output information to the context of a particular cell line. If one accepts the Lamb precept that cell line does not matter then this limitation may be benign.

However, agents suitable as pharmaceutical agents and agents suitable as cosmetic agents are categorically distinct, with the former defining agents selected for specificity and which are intended to have measurable effects on structure and function of the body, while the latter are selected for effect on appearance and may not effect structure and function of the body to a measurable degree. Cosmetic agents tend to be non-specific with respect to effect on cellular phenotype, and administration to the body is generally limited to application on or close to the body surface.

In constructing C-maps relating to pharmaceutical agents, Lamb stresses that particular difficulty is encountered if reference connections are extremely sensitive and at the same time difficult to detect (weak), and Lamb adopted compromises aimed at minimizing numerous, diffuse associations. Since the regulatory scheme for drug products requires high degrees of specificity between a purported drug agent and disease state, and modulation of disease by impacting a single protein with a minimum of tangential associations is desired in development of pharmaceutical actives, the Lamb C-map is well-suited for screening for potential pharmaceutical agents despite the noted compromises.

The connectivity mapping protocols of Lamb would not be predicted, therefore, to have utility for hypothesis testing/generating in the field of cosmetics. Cosmetic formulators seek agents or compositions of agents capable of modulating multiple targets and having effects across complex phenotypes and conditions. Further, the phenotypic impact of a cosmetic agent must be relatively low by definition, so that the agent avoids being subject to the regulatory scheme for pharmaceutical actives. Nonetheless, the impact must be perceptible to the consumer and preferably empirically confirmable by scientific methods. Gene transcription/expression profiles for cosmetic conditions are generally diffuse, comprising many genes with low to moderate fold differentials. Cosmetic agents, therefore, provide more diverse and less acute effects on cellular phenotype and generate the sort of associations expressly taught by Lamb as unsuitable for generating connectivity maps useful for confident hypothesis testing.

Nonetheless, contrary to the teachings of Lamb and the prior art in general, the present inventors surprisingly discovered that useful connectivity maps could be developed from cosmetic active—cellular phenotype—gene expression data associations in particular with respect to skin-care actives and cosmetic agents, despite the highly diffuse, systemic and low-level effects these sorts of actives generally engender. Further, contrary to assertions by the Lamb team that results should be substantially independent of cell-type, the present invention is based in part on the surprising discovery that selection of human epidermal keratinocyte cells as the relevant cell line resulted in construction of connectivity maps particularly useful for hypothesis generating and testing relating to skin-active agents and cosmetic agents useful in the treatment of dandruff.

As noted above, the dandruff condition is particularly complex and its etiology is not fully understood. The present investigators therefore made a novel adaptation to the C-map paradigm that has proven to be particularly useful in identifying agents with potential efficacy in certain skin diseases, including dandruff. Although gene expression signatures are determined for the skin condition, the gene expression signature is further analyzed to determine an implicated biological process pattern which is used to derive a physiological thematic expression signature. The theme signature is then used to query the C-map data base to generate a skin-active agent output where highly negative connectivity to the skin condition thematic expression signature predicts efficacy for treatment of the skin condition. To the best knowledge of the present investigators, application of connectivity mapping to target a multi-factored, poorly delineated and low-level "disease" condition such as dandruff, by identifying agents through the use of physiological theme expression signatures has not been attempted previously.

The present investigators further discovered that a well-designed connectivity map may provide insights into the pathogenesis of the skin condition and the mechanism of action of benchmark actives. By application of C-map, the present inventors surprisingly discovered, for example, modes of action for anti-fungal agents that are independent of anti-fungal properties. Further, by conducting the transcriptional profiling analyses as part of the C-map process, the present inventors surprisingly discovered that by inspecting a gene expression signature for biological process themes, in vitro models of disease states could be constructed with a surprisingly high fidelity to the clinical disease state with respect to response of the gene expression profile to specific skin-active agents.

Successful identification of anti-dandruff agents has proven to be difficult due to the multi-cellular, multi-factorial processes involved in etiology of the dandruff condition itself. Conventional in vitro studies of biological responses to potential anti-dandruff agents can be hindered by the complex or weakly detectable responses typically induced and/or caused by the putative or potential agents. Such weak responses arise, in part, due to the great number of genes and gene products involved, and skin-active and cosmetic agents may affect multiple genes in multiple ways. Moreover, the degree of bioactivity of cosmetic agents may differ for each gene and be difficult to quantify.

The value of a connectivity map approach to discover functional connections among cosmetic phenotypes such as aged skin, gene expression perturbation, and cosmetic agent action is counter-indicated by the progenitors of the drug-based C-map. The relevant phenotypes are very complex, the genetic perturbations are numerous and weak, and cosmetic agent action is likewise diffuse and by definition, relatively weak. It was considered unlikely that statistically valid data could be generated from cosmetic C-maps and it was unclear whether a cell line existed which could provide salient or detectable cosmetic data.

SUMMARY OF THE INVENTION

Surprisingly, the present inventors have developed a C-map approach to the discovery of skin-active agents having efficacy for particular skin disorders such as dandruff, and which may also be useful for revealing insights into the pathogenesis of the disease and mechanism of action of selected agents.

Accordingly, the present invention provides novel methods, systems and models useful for generating potential new skin-active agents efficacious for the treatment of skin conditions such as dandruff. Through careful selection of cell type, and by generation of a reference collection of gene-expression profiles for known skin-active agents and recognized skin disorders, along with determination of physiological theme expression signatures, the present inventors were surprisingly able to create a connectivity map architecture useful for testing and generating hypotheses about skin-active agents and skin disorders. The present investigators further applied the novel connectivity map protocol to develop an in vitro model of a skin disorder which may be used to test putative or potential skin-active agents and/or to investigate the functional mechanism of a known active.

The present invention provides embodiments which broadly include methods and systems for determining relationships between a skin condition/disorder of interest and one or more skin-active agents, one or more genes associated with the skin disorder condition, and physiological themes implicated by the skin condition and/or affected by a skin-active agent. The inventive methods may be used to identify skin-active agents without detailed knowledge of the mechanisms of biological processes associated with a skin disorder or condition of interest, all of the genes associated with such a condition, or the cell types associated with such a condition.

According to one embodiment of the invention, a method for constructing a data architecture for use in identifying connections between perturbagens and genes associated with one or more skin conditions is provided. The method comprises: (a) providing a gene expression profile for a control human epidermal keratinocyte cell; (b) generating a gene expression profile for a human epidermal keratinocyte cell exposed to at least one perturbagen; (c) identifying genes differentially expressed in response to the at least one perturbagen by comparing the gene expression profiles of (a) and (b); (d) creating an ordered list comprising identifiers representing the differentially expressed genes, wherein the identifiers are ordered according to the differential expression of the genes; (e) storing the ordered list as a keratinocyte instance on at least one computer readable medium; and (f) constructing a data architecture of stored keratinocyte instances by repeating (a) through (e), wherein the at least one perturbagen of step (a) is different for each keratinocyte instance. According to another embodiment, a method for generating a gene expression signature for use in identifying connections between perturbagens and genes associated with a dandruff condition is provided. The method comprises: (a) providing a gene expression profile for a reference sample of human scalp skin cells; (b) generating a gene expression profile for at least one sample of human scalp skin cells from a subject exhibiting a dandruff condition, (c) comparing the expression profiles of (a) and (b) to determine a gene expression signature comprising a set of genes differentially expressed in (a) and (b); (d) assigning an identifier to each gene constituting the gene expression signature and ordering the identifiers according to the direction of differential expression to create one or more gene expression signature lists; and (e) storing the one or more gene expression signature lists on at least one computer readable medium.

The inventive data architecture may be provided on a computer readable medium. The computer readable medium comprises a first digital file stored in a spreadsheet file format, a word processing file format, or a database file format suitable to be read by a respective spreadsheet, word processing, or database computer program, the first digital file comprising data arranged to provide one or more gene expression signature lists comprising a plurality of identifiers when read by the respective spreadsheet, word processing, or database computer program; and wherein each identifier is selected from the group consisting of a microarray probe set ID, a human gene name, a human gene symbol, and combinations thereof representing a gene set identified as regulated in the gene expression signature, and wherein the gene expression signature list comprises between about 50 and about 600 identifiers.

A further embodiment is directed to a method for identifying a skin-active agent having predictable efficacy in treatment of a skin condition. The method comprises: a. determining a gene expression signature for the skin condition wherein the gene expression signature comprises genes significantly up- and down-regulated in a skin sample affected with the skin condition when compared to skin not affected with the skin condition; b. determining a thematic expression signature for the skin condition by mapping the gene expression signature on a biological processes grid, such as the Gene Ontology, to determine one or more regulated processes, wherein a theme expression signature reflects statistical clustering of the regulated processes; c. providing a connectivity map data architecture according to the invention; d. querying the connectivity map with the thematic expression signature determined in (b) to generate an output of skin-active agents; and e. rank-ordering the output by connectivity score wherein a negative connectivity score predicts efficacy of a skin-active agent for the treatment of the skin condition.

In vitro models of a skin disease and methods for constructing them are also disclosed. The models are useful for evaluating clinical efficacy of proposed therapeutic agents in treatment of the skin disease. The method comprises: a. determining a gene expression signature for the disease state wherein the gene expression signature comprises genes significantly up and down regulated in the disease; b. conducting a biological process analysis of the regulated genes to identify biological processes implicated by the regulated genes; c. treating a skin culture to simulate the biological processes identified in (b); d. confirming validity of the in vitro model of the skin disease by determining the gene expression signature for the treated skin culture and assessing the degree to which it mimics the gene signature determined in (a).

In other aspects, the invention provides inventive gene expression signatures which may exist tangibly in various forms known in the art. For example, a gene expression signature may exist as a set of immobilized oligonucleotides wherein each oligonucleotide uniquely hybridizes to a nucleotide sequence identifying a region of a gene in the signature. It is understood that the "genes set forth" in a table refers to gene identifiers designating the genes, and that a gene expression signature as set forth herein is set forth according to a gene identifier.

These and additional objects, embodiments, and aspects of the invention will become apparent by reference to the Figures and Detailed Description below.

BRIEF DESCRIPTION OF THE FIGURES

FIG. 1A and FIG. 1B sets forth the genes constituting two different gene expression signatures for dandruff-affected skin. Table B includes the 70 most significantly up- and down-regulated genes as the dandruff gene expression signature, and Table A sets forth the most significantly up- and down-regulated genes in the gene clusters (Lipid Metabolism and Immune Function) defining a thematic profile for dandruff.

FIG. 9 includes a table showing a broad-pattern physiological theme gene expression pattern for Dandruff vs. non-dandruff.

FIG. 18 includes a table and summarizes the transcriptomics study design for analysis of the mechanism of ZPT according to an inventive method.

FIG. 20 depicts a heat map showing the effect of ZPT on the physiological thematic signature for dandruff.

FIG. 21A and FIG. 21B illustrates that a high fidelity in vitro model of dandruff may be constructed by treating a skin culture with a combination of IL17 and IL22.

DETAILED DESCRIPTION OF THE INVENTION

Figure 2:
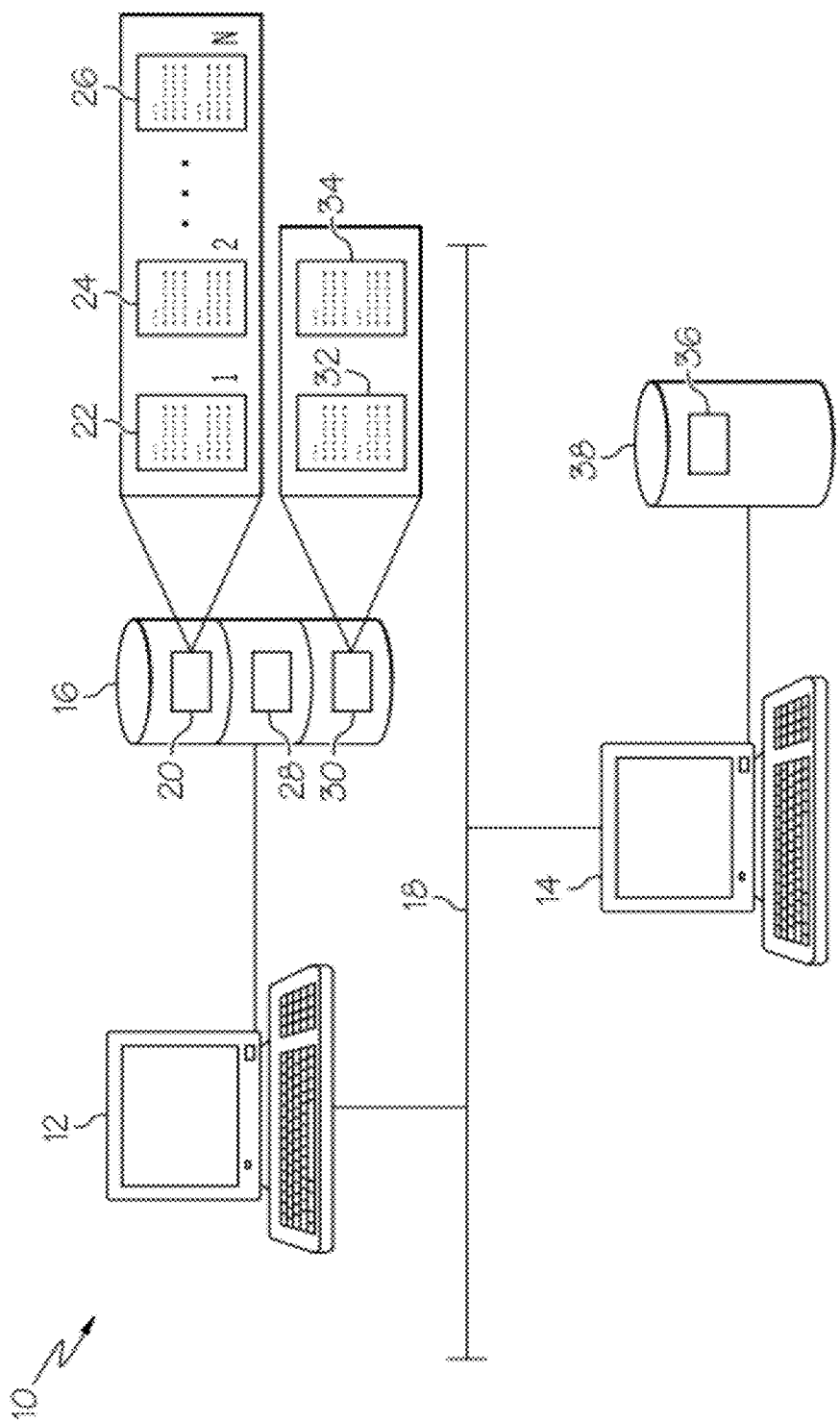
FIG. 2 is a schematic illustration of a computer system suitable for use with the present invention.

The present invention will now be described with occasional reference to the specific embodiments of the invention. This invention may, however, be embodied in different forms and should not be construed as limited to the embodiments set forth herein. Rather, these embodiments are provided so that this disclosure will be thorough and complete, and to fully convey the scope of the invention to those skilled in the art.

Unless otherwise defined, all technical and scientific terms used herein have the same meaning as commonly understood by one of ordinary skill in the art to which this invention pertains. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

As used interchangeably herein, the terms "connectivity map" and "C-map" refer broadly to devices, systems, articles of manufacture, and methodologies for identifying relationships between cellular phenotypes or cosmetic conditions, gene expression, and perturbagens, such as cosmetic actives.

As used herein, the term "cosmetic agent" means any substance, as well as any component thereof, intended to be rubbed, poured, sprinkled, sprayed, introduced into, or otherwise applied to a mammalian body or any part thereof for purposes of cleansing, beautifying, promoting attractiveness, altering the appearance, or combinations thereof. Cosmetic agents may include substances that are Generally Recognized as Safe (GRAS) by the US Food and Drug Administration, food additives, and materials used in non-cosmetic consumer products including over-the-counter medications. In some embodiments, cosmetic agents may be incorporated in a cosmetic composition comprising a dermatologically acceptable carrier suitable for topical application to skin. A cosmetic agent includes, but is not limited to, (i) chemicals, compounds, small or large molecules, extracts, formulations, or combinations thereof that are known to induce or cause at least one effect (positive or negative) on skin tissue; (ii) chemicals, compounds, small molecules, extracts, formulations, or combinations thereof that are known to induce or cause at least one effect (positive or negative) on skin tissue and are discovered, using the provided methods and systems, to induce or cause at least one previously unknown effect (positive or negative) on the skin tissue; and (iii) chemicals, compounds, small molecules, extracts, formulations, or combinations thereof that are not known have an effect on skin tissue and are discovered, using the provided methods and systems, to induce or cause an effect on skin tissue.

Some examples of cosmetic agents or cosmetically actionable materials can be found in: the PubChem database associated with the National Institutes of Health, USA (http://pubchem.ncbi.nlm.nih.gov); the Ingredient Database of the Personal Care Products Council (http://online.personalcarecouncil.org/jsp/Home.jsp); and the 2010 International Cosmetic Ingredient Dictionary and Handbook, 13$^{th}$ Edition, published by The Personal Care Products Council; the EU Cosmetic Ingredients and Substances list; the Japan Cosmetic Ingredients List; the Personal Care Products Council, the SkinDeep database (URL: http://www.cosmeticsdatabase.com); the FDA Approved Excipients List; the FDA OTC List; the Japan Quasi Drug List; the US FDA Everything Added to Food database; EU Food Additive list; Japan Existing Food Additives, Flavor GRAS list; US FDA Select Committee on GRAS Substances; US Household Products Database; the Global New Products Database (GNPD) Personal Care, Health Care, Food/Drink/Pet and Household database (URL: http://www.gnpd.com); and from suppliers of cosmetic ingredients and botanicals.

Other non-limiting examples of cosmetic agents include botanicals (which may be derived from one or more of a root, stem bark, leaf, seed or fruit of a plant). Some botanicals may be extracted from a plant biomass (e.g., root, stem, bark, leaf, etc.) using one more solvents. Botanicals may comprise a complex mixture of compounds and lack a distinct active ingredient. Another category of cosmetic agents are vitamin compounds and derivatives and combinations thereof, such as a vitamin B3 compound, a vitamin B5 compound, a vitamin B6 compound, a vitamin B9 compound, a vitamin A compound, a vitamin C compound, a vitamin E compound, and derivatives and combinations thereof (e.g., retinol, retinyl esters, niacinamide, folic acid, panethenol, ascorbic acid, tocopherol, and tocopherol acetate). Other non-limiting examples of cosmetic agents include sugar amines, phytosterols, hexamidine, hydroxy acids, ceramides, amino acids, and polyols.

As used herein, the term "skin-active agent" is a subset of cosmetic agents as defined herein and includes generally any substance, as well as any component thereof, intended to be applied to the skin for the purpose of effectuating a treatment of an undesirable skin condition, for example, dandruff, seborrheic dermatitis, atopic dermatitis, rash, acne, or other condition that may be of substantially cosmetic concern. Categorical examples of skin-active agents include anti-dandruff actives, steroidal anti-inflammatory agents, non-steroidal anti-inflammatory agents, pediculocides, sensates, enzymes, vitamins, hair growth actives, sunscreens, and combinations thereof. Cosmetic compositions according to the instant invention may contain skin-active agents.

A specific category of skin-active agent is an anti-dandruff agent. Anti-dandruff agents known in the art include an antimicrobial anti-dandruff active, concentrations of which within the compositions range from about 0.001% to about 5%, more preferably from about 0.01% to about 3%, even more preferably from about 0.05% to about 1%, by weight of the composition. Specific examples of antimicrobial anti-dandruff actives include antifungal actives such as pyrithione salts, octopirox, ketoconazole, climbazole, ciclopirox, terbinafine, and sulfur or sulfur-containing actives such as selenium sulfide. A very specific example is zinc pyrithione (ZPT) at concentrations ranging from 0.005% to 2%, more preferably from about 0.005% to about 0.5%, by weight of the composition. Selenium sulfides are antimicrobial anti-dandruffs active well known in the personal care arts and are described, for example, in U.S. Pat. No. 2,694,668; U.S. Pat. No. 3,152,046; U.S. Pat. No.

4,089,945; and U.S. Pat. No. 4,885,107, which disclosures are incorporated in their entirety herein by this reference.

Pyrithione antimicrobial actives, especially 1-hydroxy-2-pyridinethione salts, are also well-known anti-dandruff actives for use in the scalp cosmetic compositions. Examples of pyrithione salts are those formed from heavy metals such as zinc, tin, cadmium, magnesium, aluminum and zirconium. Zinc salts are particularly favored anti-dandruff agents, especially the zinc salt of 1-hydroxy-2-pyridinethione (zinc pyrithione, ZPT). Other cations such as sodium may also be suitable. Pyrithione antimicrobial actives are well known in the hair care art and are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982, the disclosures of which are incorporated in their entirety herein by this reference. Other specific examples of zinc-containing skin-active agents which may be suitable as anti-dandruff agents include zinc pyrithione, zinc acetate, zinc acetylmethionate, zinc aspartate, zinc borate, zinc carbonate, zinc chloride, zinc citrate, zinc DNA, zinc formaldehyde sulfoxylate, zinc gluconate, zinc glutamate, zinc hydrolyzed collagen, zinc lactate, zinc laurate, zinc myristate, zinc neodecanoate, zinc palmitate, zinc PCA, zinc pentadecene tricarboxylate, zinc ricinoleate, zinc rosinate, zinc stearate, zinc sulfate, zinc undecylenate, zinc oxide, zinc lactobionate, and combinations thereof.

The terms "gene expression signature," and "gene-expression signature" refer to a rationally derived list, or plurality of lists, of genes representative of a skin tissue condition or a skin agent. In specific contexts, the skin agent may be a benchmark skin agent or a potential skin agent. Thus, the gene expression signature may serve as a proxy for a phenotype of interest for skin tissue. A gene expression signature may comprise genes whose expression, relative to a normal or control state, is increased (up-regulated), whose expression is decreased (down-regulated), and combinations thereof. Generally, a gene expression signature for a modified cellular phenotype may be described as a set of genes differentially expressed in the modified cellular phenotype over the cellular phenotype. A gene expression signature can be derived from various sources of data, including but not limited to, from in vitro testing, in vivo testing and combinations thereof. In some embodiments, a gene expression signature may comprise a first list representative of a plurality of up-regulated genes of the condition of interest and a second list representative of a plurality of down-regulated genes of the condition of interest.

As used herein, the term "benchmark skin agent" refers to any chemical, compound, small or large molecule, extract, formulation, or combinations thereof that is known to induce or cause a superior effect (positive or negative) on skin tissue. Non-limiting examples of benchmark skin-active agents well-known in the dandruff arts include Zinc pyrithione (ZPT), Selenium sulfide, ketoconazole, Ciclopirox olamine and tar. Zinc pyrithione is commonly known as an antifungal and antibacterial agent and was first reported in the 1930s. Zinc pyrithione is best known for its use in the treatment of dandruff and seborrheic dermatitis. It also has antibacterial properties and is effective against many pathogens from the streptococcus and staphylococcus class. Its other medical applications include treatments of psoriasis, eczema, ringworm, fungus, athlete's foot, dry skin, atopic dermatitis, tinea, and vitiligo. Selenium sulfide is available as a 1% and 2.5% lotion and shampoo. In some countries, the higher strength preparations require a doctor's prescription. The shampoo is used to treat dandruff and seborrhea of the scalp, and the lotion is used to treat tinea versicolor, a fungal infection of the skin. Tar is a skin-active agent known to be effective as a therapeutic treatment to control scalp itching and flaking symptomatic of scalp psoriasis, eczema, seborrheic dermatitis and dandruff.

As used herein, the term "query" refers to data that is used as an input to a Connectivity Map and against which a plurality of instances are compared. A query may include a gene expression signature associated with a skin condition such as dandruff, or may include a gene expression signature derived from a physiological process signature determined for a skin condition. A C-map may be queried with perturbagens, gene expression signatures, skin disorders, thematic signatures, or any data feature or combination of data features or associations that comprise the data architecture.

The term "instance," as used herein, refers to data from a gene expression profiling experiment in which skin cells are dosed with a perturbagen. In some embodiments, the data comprises a list of identifiers representing the genes that are part of the gene expression profiling experiment. The identifiers may include gene names, gene symbols, microarray probe set IDs, or any other identifier. In some embodiments, an instance may comprise data from a microarray experiment and comprises a list of probe set IDs of the microarray ordered by their extent of differential expression relative to a control. The data may also comprise metadata, including but not limited to data relating to one or more of the perturbagen, the gene expression profiling test conditions, the skin cells, and the microarray.

The term "keratinous tissue," as used herein, refers to keratin-containing layers disposed as the outermost protective covering of mammals which includes, but is not limited to, skin, hair, nails, cuticles, horns, claws, beaks, and hooves. With respect to skin, the term refers to one or all of the dermal, hypodermal, and epidermal layers, which includes, in part, keratinous tissue.

As used herein, the term "dandruff" refers to a condition of scalp marked by excessive flaking of scalp skin and typically accompanied by itching, regardless of etiology or pathogenic mechanism. Dandruff is distinguished from seborrheic dermatitis by the presence of affected skin outside the scalp in seborrheic dermatitis. The term "dandruff" may also refer to the flake itself.

The term "perturbagen," as used herein, means anything used as a challenge in a gene expression profiling experiment to generate gene expression data for use in the present invention. In some embodiments, the perturbagen is applied to keratinocyte cells and the gene expression data derived from the gene expression profiling experiment may be stored as an instance in a data architecture. Any substance, chemical, compound, active, natural product, extract, drug [e.g. Sigma-Aldrich LOPAC (Library of Pharmacologically Active Compounds) collection], small molecule, and combinations thereof used as to generate gene expression data can be a perturbagen. A perturbagen can also be any other stimulus used to generate differential gene expression data. For example, a perturbagen may also be UV radiation, heat, osmotic stress, pH, a microbe, a virus, a recombinant cytokine or growth factor, or small interfering RNA. A perturbagen may be, but is not required to be, any cosmetic agent.

The term "dermatologically acceptable," as used herein, means that the compositions or components described are suitable for use in contact with human skin tissue without undue toxicity, incompatibility, instability, allergic response, and the like.

As used herein, the term "computer readable medium" refers to any electronic storage medium and includes but is not limited to any volatile, nonvolatile, removable, and non-removable media implemented in any method or technology for storage of information such as computer readable instructions, data and data structures, digital files, software programs and applications, or other digital information. Computer readable media includes, but are not limited to, application-specific integrated circuit (ASIC), a compact disk (CD), a digital versatile disk (DVD), a random access memory (RAM), a synchronous RAM (SRAM), a dynamic RAM (DRAM), a synchronous DRAM (SDRAM), double data rate SDRAM (DDR SDRAM), a direct RAM bus RAM (DRRAM), a read only memory (ROM), a programmable read only memory (PROM), an electronically erasable programmable read only memory (EEPROM), a disk, a carrier wave, and a memory stick. Examples of volatile memory include, but are not limited to, random access memory (RAM), synchronous RAM (SRAM), dynamic RAM (DRAM), synchronous DRAM (SDRAM), double data rate SDRAM (DDR SDRAM), and direct RAM bus RAM (DRRAM). Examples of non-volatile memory include, but are not limited to, read only memory (ROM), programmable read only memory (PROM), erasable programmable read only memory (EPROM), and electrically erasable programmable read only memory (EEPROM). A memory can store processes and/or data. Still other computer readable media include any suitable disk media, including but not limited to, magnetic disk drives, floppy disk drives, tape drives, Zip drives, flash memory cards, memory sticks, compact disk ROM (CD-ROM), CD recordable drive (CD-R drive), CD rewriteable drive (CD-RW drive), and digital versatile ROM drive (DVD ROM).

As used herein, the terms "software" and "software application" refer to one or more computer readable and/or executable instructions that cause a computing device or other electronic device to perform functions, actions, and/or behave in a desired manner. The instructions may be embodied in one or more various forms like routines, algorithms, modules, libraries, methods, and/or programs. Software may be implemented in a variety of executable and/or loadable forms and can be located in one computer component and/or distributed between two or more communicating, co-operating, and/or parallel processing computer components and thus can be loaded and/or executed in serial, parallel, and other manners. Software can be stored on one or more computer readable medium and may implement, in whole or part, the methods and functionalities of the present invention.

As used herein, the term "dandruff gene expression signature" refers to a gene expression signature derived from gene expression profiling of a dandruff condition.

As used herein, the term "connectivity score" refers to a derived value representing the degree to which an instance correlates to a query.

As used herein, the term "data architecture" refers generally to one or more digital data structures comprising an organized collection of data. In some embodiments, the digital data structures can be stored as a digital file (e.g., a spreadsheet file, a text file, a word processing file, a database file, etc.) on a computer readable medium. In some embodiments, the data architecture is provided in the form of a database that may be managed by a database management system (DBMS) that is be used to access, organize, and select data (e.g., instances and gene expression signatures) stored in a database.

As used herein, the terms "gene expression profiling" and "gene expression profiling experiment" refer to the measurement of the expression of multiple genes in a biological sample using any suitable profiling technology. For example, the mRNA expression of thousands of genes may be determined using microarray techniques. Other emerging technologies that may be used include RNA-Seq or whole transcriptome sequencing using NextGen sequencing techniques.

As used herein, the term "microarray" refers broadly to any ordered array of nucleic acids, oligonucleotides, proteins, small molecules, large molecules, and/or combinations thereof on a substrate that enables gene expression profiling of a biological sample. Non-limiting examples of microarrays are available from Affymetrix, Inc.; Agilent Technologies, Inc.; Ilumina, Inc.; GE Healthcare, Inc.; Applied Biosystems, Inc.; Beckman Coulter, Inc.; etc.

Unless otherwise indicated, all numbers expressing quantities of ingredients, properties such as molecular weight, reaction conditions, and so forth as used in the specification and claims are to be understood as being modified in all instances by the term "about". Additionally, the disclosure of any ranges in the specification and claims are to be understood as including the range itself and also anything subsumed therein, as well as endpoints. All numeric ranges are inclusive of narrower ranges; delineated upper and lower range limits are interchangeable to create further ranges not explicitly delineated. Unless otherwise indicated, the numerical properties set forth in the specification and claims are approximations that may vary depending on the desired properties sought to be obtained in embodiments of the present invention. Notwithstanding that numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

In accordance with one aspect of the present invention, provided are devices, systems and methods for implementing a connectivity map utilizing one or more query signatures associated with a dandruff or a dandruff-related condition. The query signatures may be derived in variety of ways. In some embodiments, the query signatures may be gene expression signatures derived from gene expression profiling of full thickness skin biopsies of skin exhibiting a skin condition of interest compared to a control. The gene expression profiling can be carried out using any suitable technology, including but not limited to microarray analysis or NextGen sequencing. An example of a gene expression signature includes a specific dandruff gene expression signature, an example of which is described more fully hereafter. A query signature may be derived from transcriptional profiling of a keratinocyte cell line exposed to benchmark skin-active agents such as anti-dandruff agents. In other embodiments, the query signature may be a physiological theme expression signature derived from an analysis of statistically over-represented Gene Ontology processes and determining statistical clustering of the regulated genes as a function of the Gene Ontology. These query signatures may be used singularly or in combination.

In accordance with another aspect of the present invention, provided are devices, systems, and methods for implementing a connectivity map utilizing one or more instances derived from a perturbagen, such as a cosmetic agent, exposed to an epidermal keratinocyte cell line. Instances from more complex cell culture systems may also be used, such as skin organotypic cultures containing keratinocytes or ex vivo human skin. Instances from a plurality of cell lines may be used with the present invention.

In accordance with yet another aspect of the present invention, provided are devices, systems and methods for identification of relationships between a skin condition, e.g. dandruff condition query signature and a plurality of instances, where the query signature may be a gene expression signature or a physiological theme expression signature. For example, it may be possible to ascertain perturbagens that give rise to a statistically significant activity on a statistically significant number of genes associated with a skin condition of interest, leading to the identification of new cosmetic agents for treating the skin condition or new uses of known cosmetic agents.

I. Systems and Devices

Figure 4:
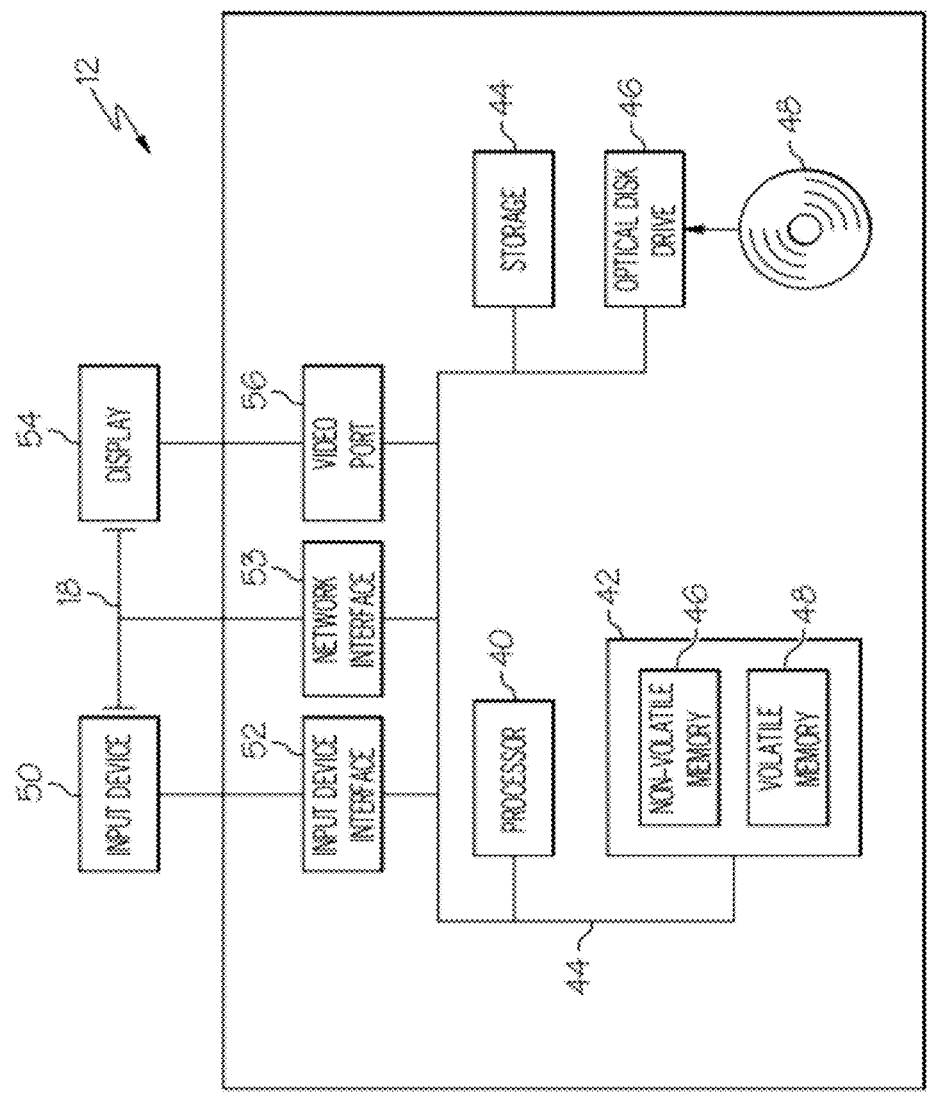
FIG. 4 is a schematic illustration of a programmable computer suitable for use with the present invention.
Figure 5:
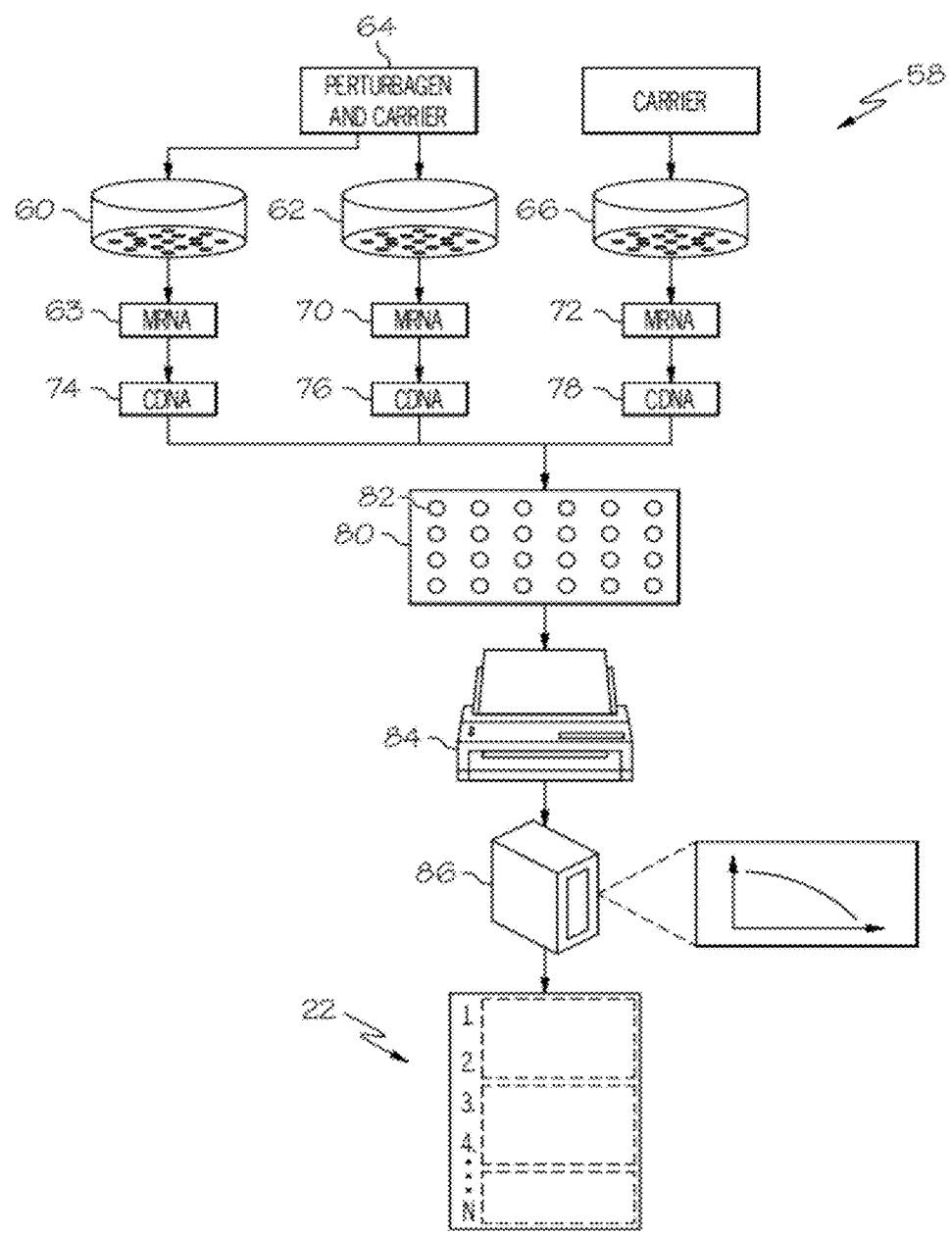
FIG. 5 is a schematic illustration of an exemplary system for generating an instance.

Referring to FIGS. 2, 4 and 5, some examples of systems and devices in accordance with the present invention for use in identifying relationships between perturbagens, skin tissue/dandruff conditions, and genes associated with the skin tissue/dandruff condition will now be described. System 10 comprises one or more of computing devices 12, 14, a computer readable medium 16 associated with the computing device 12, and communication network 18.

The computer readable medium 16, which may be provided as a hard disk drive, comprises a digital file 20, such as a database file, comprising a plurality of instances 22, 24, and 26 stored in a data structure associated with the digital file 20. The plurality of instances may be stored in relational tables and indexes or in other types of computer readable media. The instances 22, 24, and 26 may also be distributed across a plurality of digital files, a single digital file 20 being described herein however for simplicity.

The digital file 20 can be provided in wide variety of formats, including but not limited to a word processing file format (e.g., Microsoft Word), a spreadsheet file format (e.g., Microsoft Excel), and a database file format. Some common examples of suitable file formats include, but are not limited to, those associated with file extensions such as *.xls, *.xld, *.xlk, *.xll, *.xlt, *.xlxs, *.dif, *.db, *.dbf, *.accdb, *.mdb, *.mdf, *.cdb, *.fdb, *.csv, *sql, *.xml, *.doc, *.txt, *.rtf, *.log, *.docx, *.ans, *.pages, *.wps, etc.

Figure 3:
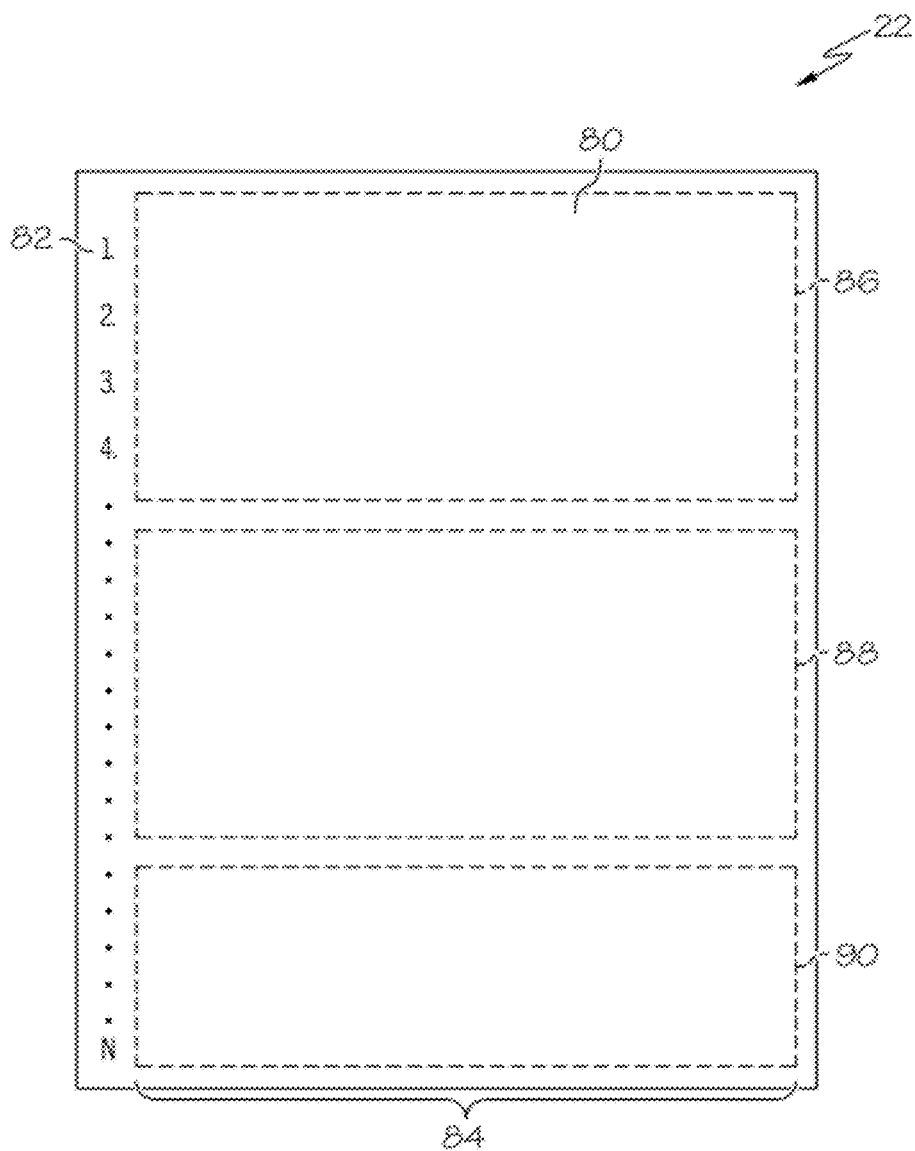
FIG. 3 is a schematic illustration of an instance associated with a computer readable medium of the computer system of FIG. 2.

Referring to FIG. 3, in some embodiments the instance 22 may comprise an ordered listing of microarray probe set IDs, wherein the value of N is equal to the total number of probes on the microarray used in analysis. Common microarrays include Affymetrix GeneChips and Illumina BeadChips, both of which comprise probe sets and custom probe sets. To generate the reference gene profiles according to the invention, preferred chips are those designed for profiling the human genome. Examples of Affymetrix chips with utility in the instant invention include model Human Genome (HG)-U133 Plus 2.0. A specific Affymetrix chip employed by the instant investigators is HG-U133A2.0, however it will be understood by a person or ordinary skill in the art that any chip or microarray, regardless of proprietary origin, is suitable so long as the probe sets of the chips used to construct a data architecture according to the invention are substantially similar.

Instances derived from microarray analyses utilizing Affymetrix GeneChips may comprise an ordered listing of gene probe set IDs where the list comprises 22,000+ IDs. The ordered listing may be stored in a data structure of the digital file 20 and the data arranged so that, when the digital file is read by the software application 28, a plurality of character strings are reproduced representing the ordered listing of probe set IDs. While it is preferred that each instance comprise a full list of the probe set IDs, it is contemplated that one or more of the instances may comprise less than all of the probe set IDs of a microarray. It is also contemplated that the instances may include other data in addition to or in place of the ordered listing of probe set IDs. For example, an ordered listing of equivalent gene names and/or gene symbols may be substituted for the ordered listing of probe set IDs. Additional data may be stored with an instance and/or the digital file 20. In some embodiments, the additional data is referred to as metadata and can include one or more of cell line identification, batch number, exposure duration, and other empirical data, as well as any other descriptive material associated with an instance ID. The ordered list may also comprise a numeric value associated with each identifier that represents the ranked position of that identifier in the ordered list.

Referring again to FIGS. 2, 3 and 4, the computer readable medium 16 may also have a second digital file 30 stored thereon. The second digital file 30 comprises one or more lists 32 of microarray probe set IDs associated with one or more dandruff gene expression signatures. The listing 32 of microarray probe set IDs typically comprises a much smaller list of probe set IDs than the instances of the first digital file 20. In some embodiments, the list comprises between 2 and 1000 probe set IDs. In other embodiments the list comprises greater than 10, 50, 100, 200, or 300 and/or less than about 800, 600, or about 400 probe set IDs. The listing 32 of probe set IDs of the second digital file 30 comprises a list of probe set IDs representing up, and/or down-regulated genes selected to represent a skin condition of interest. In some embodiments, a first list may represent the up-regulated genes and a second list may represent the down-regulated genes of the gene expression signature. The listing(s) may be stored in a data structure of the digital file 30 and the data arranged so that, when the digital file is read by the software application 28, a plurality of character strings are reproduced representing the list of probe set IDs. Instead of probe set IDs, equivalent gene names and/or gene symbols (or another nomenclature) may be substituted for a list of probe set IDs. Additional data may be stored with the gene expression signature and/or the digital file 30 and this is commonly referred to as metadata, which may include any associated information, for example, cell line or sample source, and microarray identification. Examples of listings of probe set IDs for a dandruff gene expression signature is set forth in Tables A (up-regulated and down-regulated genes clustered in a physiological theme signature/pattern) and B (the 70 most up-regulated and 70 most down-regulated genes in a dandruff gene expression signature). In some embodiments, one or more skin condition/dandruff gene expression signatures may be stored in a plurality of digital files and/or stored on a plurality of computer readable media. In other embodiments, a plurality of gene expression signatures (e.g., 32, 34) may be stored in the same digital file (e.g., 30) or stored in the same digital file or database that comprises the instances 22, 24, and 26.

As previously described, the data stored in the first and second digital files may be stored in a wide variety of data structures and/or formats. In some embodiments, the data is stored in one or more searchable databases, such as free databases, commercial databases, or a company's internal proprietary database. The database may be provided or structured according to any model known in the art, such as for example and without limitation, a flat model, a hierarchical model, a network model, a relational model, a dimensional model, or an object-oriented model. In some embodiments, at least one searchable database is a company's internal proprietary database. A user of the system 10 may use a graphical user interface associated with a database management system to access and retrieve data from the one or more databases or other data sources to which the system is operably connected. In some embodiments, the first digital file 20 is provided in the form of a first database and the second digital file 30 is provided in the form of a second database. In other embodiments, the first and second digital files may be combined and provided in the form of a single file.

In some embodiments, the first digital file 20 may include data that is transmitted across the communication network 18 from a digital file 36 stored on the computer readable medium 38. In one embodiment, the first digital file 20 may comprise gene expression data obtained from a cell line (e.g., a fibroblast cell line and/or a keratinocyte cell line) as well as data from the digital file 36, such as gene expression data from other cell lines or cell types, gene expression signatures, perturbagen information, clinical trial data, scientific literature, chemical databases, pharmaceutical databases, and other such data and metadata. The digital file 36 may be provided in the form of a database, including but not limited to Sigma-Aldrich LOPAC collection, Broad Institute C-MAP collection, GEO collection, and Chemical Abstracts Service (CAS) databases.

The computer readable medium 16 (or another computer readable media, such as 16) may also have stored thereon one or more digital files 28 comprising computer readable instructions or software for reading, writing to, or otherwise managing and/or accessing the digital files 20, 30. The computer readable medium 16 may also comprise software or computer readable and/or executable instructions that cause the computing device 12 to perform one or more steps of the methods of the present invention, including for example and without limitation, the step(s) associated with comparing a gene expression signature stored in digital file 30 to instances 22, 24, and 26 stored in digital file 20. In some embodiments, the one or more digital files 28 may form part of a database management system for managing the digital files 20, 28. Non-limiting examples of database management systems are described in U.S. Pat. Nos. 4,967, 341 and 5,297,279.

The computer readable medium 16 may form part of or otherwise be connected to the computing device 12. The computing device 12 can be provided in a wide variety of forms, including but not limited to any general or special purpose computer such as a server, a desktop computer, a laptop computer, a tower computer, a microcomputer, a mini computer, and a mainframe computer. While various computing devices may be suitable for use with the present invention, a generic computing device 12 is illustrated in FIG. 4. The computing device 12 may comprise one or more components selected from a processor 40, system memory 42, and a system bus 44. The system bus 44 provides an interface for system components including but not limited to the system memory 42 and processor 40. The system bus 36 can be any of several types of bus structures that may further interconnect to a memory bus (with or without a memory controller), a peripheral bus, and a local bus using any of a variety of commercially available bus architectures. Examples of a local bus include an industrial standard architecture (USA) bus, a microchannel architecture (MSA) bus, an extended ISA (EISA) bus, a peripheral component interconnect (PCI) bus, a universal serial (USB) bus, and a small computer systems interface (SCSI) bus. The processor 40 may be selected from any suitable processor, including but not limited to, dual microprocessor and other multi-processor architectures. The processor executes a set of stored instructions associated with one or more program applications or software.

The system memory 42 can include non-volatile memory 46 (e.g., read only memory (ROM), erasable programmable read only memory (EPROM), electrically erasable programmable read only memory (EEPROM), etc.) and/or volatile memory 48 (e.g., random access memory (RAM)). A basic input/output system (BIOS) can be stored in the non-volatile memory 38, and can include the basic routines that help to transfer information between elements within the computing device 12. The volatile memory 48 can also include a high-speed RAM such as static RAM for caching data.

The computing device 12 may further include a storage 44, which may comprise, for example, an internal hard disk drive [HDD, e.g., enhanced integrated drive electronics (EIDE) or serial advanced technology attachment (SATA)] for storage. The computing device 12 may further include an optical disk drive 46 (e.g., for reading a CD-ROM or DVD-ROM 48). The drives and associated computer-readable media provide non-volatile storage of data, data structures and the data architecture of the present invention, computer-executable instructions, and so forth. For the computing device 12, the drives and media accommodate the storage of any data in a suitable digital format. Although the description of computer-readable media above refers to an HDD and optical media such as a CD-ROM or DVD-ROM, it should be appreciated by those skilled in the art that other types of media which are readable by a computer, such as Zip disks, magnetic cassettes, flash memory cards, cartridges, and the like may also be used, and further, that any such media may contain computer-executable instructions for performing the methods of the present invention.

A number of software applications can be stored on the drives 44 and volatile memory 48, including an operating system and one or more software applications, which implement, in whole or part, the functionality and/or methods described herein. It is to be appreciated that the embodiments can be implemented with various commercially available operating systems or combinations of operating systems. The central processing unit 40, in conjunction with the software applications in the volatile memory 48, may serve as a control system for the computing device 12 that is configured to, or adapted to, implement the functionality described herein.

A user may be able to enter commands and information into the computing device 12 through one or more wired or wireless input devices 50, for example, a keyboard, a pointing device, such as a mouse (not illustrated), or a touch screen. These and other input devices are often connected to the central processing unit 40 through an input device interface 52 that is coupled to the system bus 44 but can be connected by other interfaces, such as a parallel port, an IEEE 1394 serial port, a game port, a universal serial bus (USB) port, an IR interface, etc. The computing device 12 may drive a separate or integral display device 54, which may also be connected to the system bus 44 via an interface, such as a video port 56.

The computing devices 12, 14 may operate in a networked environment across network 18 using a wired and/or wireless network communications interface 58. The network interface port 58 can facilitate wired and/or wireless communications. The network interface port can be part of a network interface card, network interface controller (NIC), network adapter, or LAN adapter. The communication network 18 can be a wide area network (WAN) such as the Internet, or a local area network (LAN). The communication network 18 can comprise a fiber optic network, a twisted-pair network, a T1/E1 line-based network or other links of the T-carrier/E carrier protocol, or a wireless local area or wide area network (operating through multiple protocols such as ultra-mobile band (UMB), long term evolution (LTE), etc.). Additionally, communication network 18 can comprise base stations for wireless communications, which include transceivers, associated electronic devices for modulation/demodulation, and switches and ports to connect to a backbone network for backhaul communication such as in the case of packet-switched communications.

II. Methods for Creating a Plurality of Instances

In some embodiments, the methods of the present invention may comprise populating at least the first digital file 20 with a plurality of instances (e.g., 22, 24, 26) comprising data derived from a plurality of gene expression profiling experiments, wherein one or more of the experiments comprise exposing, for example, keratinocyte cells (or other skin cells such as human skin equivalent cultures or ex vivo cultured human skin) to at least one perturbagen. For simplicity of discussion, the gene expression profiling discussed hereafter will be in the context of a microarray experiment.

Referring to FIG. 5, one embodiment of a method of the present invention is illustrated. The method 58 comprises exposing a keratinocyte cell to a perturbagen 64. The perturbagen may be dissolved in a carrier, such as dimethyl sulfoxide (DMSO). After exposure, mRNA is extracted from the cells exposed to the perturbagen and reference cells 66 (e.g., keratinocyte cells) which are exposed to only the carrier. The mRNA 68, 70, 72 may be reverse transcribed to cDNA 64, 76, 78 and marked with different fluorescent dyes (e.g., red and green) if a two color microarray analysis is to be performed. Alternatively, the samples may be prepped for a one color microarray analysis, and further a plurality of replicates may be processed if desired. The cDNA samples may be co-hybridized to the microarray 80 comprising a plurality of probes 82. The microarray may comprise thousands of probes 82. In some embodiments, there are between 10,000 and 50,000 gene probes 82 present on the microarray 80. The microarray is scanned by a scanner 84, which excites the dyes and measures the amount fluorescence. A computing device 86 may be used to analyze the raw images to determine the expression levels of a gene in the cells 60, 62 relative to the reference cells 66. The scanner 84 may incorporate the functionality of the computing device 86. The expression levels include: i) up-regulation [e.g., greater binding of the test material (e.g., cDNA 74, 76) to the probe than the reference material (e.g., cDNA 78)], or ii) down-regulation [e.g., greater binding of the reference material (e.g., cDNA 78) to the probe than the test material (e.g., cDNA 74, 76)], iii) expressed but not differentially [e.g., similar binding of the reference material (e.g., cDNA 78) to the probe than the test material (e.g., cDNA 74. 76)], and iv) no detectable signal or noise. The up- and down-regulated genes are referred to as differentially expressed. Microarrays and microarray analysis techniques are well known in the art, and it is contemplated that other microarray techniques may be used with the methods, devices and systems of the present invention. For example, any suitable commercial or non-commercial microarray technology and associated techniques may used. Good results have been obtained with Affymetrix GeneChip® technology and Illumina BeadChip™ technology. One illustrative technique is described in the Examples, "Generally Applicable" methods section. However, one of skill in the art will appreciate that the present invention is not limited to the methodology of the example and that other methods and techniques are also contemplated to be within its scope.

In a very specific embodiment, an instance consists of the rank ordered data for all of the probe sets on the Affymetrix HG-U133A2.0 GeneChip wherein each probe on the chip has a unique probe set IDentifier. The probe sets are rank ordered by the fold change relative to the controls in the same C-map batch (single instance/average of controls). The probe set IDentifiers are rank-ordered to reflect the most up-regulated to the most down-regulated.

Notably, even for the non-differentially regulated genes the signal values for a particular probe set are unlikely to be identical for the instance and control so a fold change different from 1 will be calculated that can be used for comprehensive rank ordering. In accordance with methods disclosed by Lamb et al. (2006), data are adjusted using 2 thresholds to minimize the effects of genes that may have very low noisy signal values, which can lead to spurious large fold changes. The thresholding is preferably done before the rank ordering. An example for illustrative purposes includes a process wherein a first threshold is set at 20. If the signal for a probe set is below 20, it is adjusted to 20. Ties for ranking are broken with a second threshold wherein the fold changes are recalculated and any values less than 2 are set to 2. For any remaining ties the order depends on the specific sorting algorithm used but is essentially random. The probe sets in the middle of the list do not meaningfully contribute to an actual connectivity score.

The rank ordered data are stored as an instance. The probes may be sorted into a list according to the level of gene expression regulation detected, wherein the list progresses from up-regulated to marginal or no regulation to down-regulated, and this rank ordered listing of probe IDs is stored as an instance (e.g., 22) in the first digital file 20. Referring to FIG. 3, the data associated with an instance comprises the probe ID 80 and a value 82 representing its ranking in the list (e.g., 1, 2, 3, 4 . . . N, where N represents the total number of probes on the microarray). The ordered list 84 may generally comprise approximately three groupings of probe IDs: a first grouping 86 of probe IDs associated with up-regulated genes, a second group 88 of probe IDs associated with genes with marginal regulation or no detectable signal or noise, and a third group 90 of probe IDs associated with down-regulated genes. The most up-regulated genes are at or near the top of the list 84 and the most down-regulated genes are at or near the bottom of the list 84. The groupings are shown for illustration, but the lists for each instance may be continuous and the number of regulated genes will depend on the strength of the effect of the perturbagen associated with the instance. Other arrangements within the list 84 may be provided. For example, the probe IDs associated with the down-regulated genes may be arranged at the top of the list 84. This instance data may also further comprise metadata such as perturbagen identification, perturbagen concentration, cell line or sample source, and microarray identification.

In some embodiments, one or more instances comprise at least about 1,000, 2,500, 5,000, 10,000, or 20,000 identifiers and/or less than about 30,000, 25,000, or 20,000 identifiers. In some embodiments, the database comprises at least about 50, 100, 250, 500, or 1,000 instances and/or less than about 50,000, 20,000, 15,000, 10,000, 7,500, 5,000, or 2,500 instances. Replicates of an instance may be created, and the same perturbagen may be used to derive a first instance from keratinocyte cells and a second instance from another skin cell type, such as fibroblasts, melanocytes or complex tissue, for example ex vivo human skin.

The present inventors have surprisingly discovered that instances derived from keratinocyte cells appear to be more predictive than other cell types when used in combination with a dandruff condition expression signature. As described more fully hereafter in Example 3, the present inventors compared instances derived from BJ fibroblast cells and keratinocyte cells with a dandruff gene expression signature and found that instances derived from the keratinocyte cells were dramatically over represented in the highest ranking results (the higher the ranking, the more likely the perturbagen is to have a beneficial affect upon the dandruff condition) compared to fibroblast cells.

III. Methods for Deriving Dandruff Gene Expression Signatures

Some methods of the present invention comprise identifying a gene expression signature that represents the up-regulated and down-regulated genes associated with a skin condition of interest, in particular with Dandruff The pathogenesis of Dandruff typically involves complex processes involving numerous known and unknown extrinsic and intrinsic factors, as well as responses to such factors that are subtle over a relatively short period of time but non-subtle over a longer period of time. This is in contrast to what is typically observed in drug development and drug screening methods, wherein a specific target, gene, or mechanism of action is of interest. Due to the unique screening challenges associated with the dandruff condition, the quality of the gene expression signature representing the condition of interest can be important for distinguishing between the gene expression data actually associated with a response to a perturbagen from the background expression data.

One challenge in developing gene expression signatures for dandruff and dandruff-related skin disorders is that the number of genes selected needs to be adequate to reflect the dominant and key biology but not so large as to include many genes that have achieved a level of statistical significance by random chance and are non-informative. Thus, query signatures should be carefully derived since the predictive value may be dependent upon the quality of the gene expression signature.

One factor that can impact the quality of the query signature is the number of genes included in the signature. The present inventors have found that, with respect to a cosmetic data architecture and connectivity map, too few genes can result in a signature that is unstable with regard to the highest scoring instances. In other words, small changes to the gene expression signature can result in significant differences in the highest scoring instance. Conversely, too many genes may tend to partially mask the dominant biological responses and will include a higher fraction of genes meeting statistical cutoffs by random chance—thereby adding undesirable noise to the signature. The inventors have found that the number of genes desirable in a gene expression signature is also a function of the strength of the biological response associated with the condition and the number of genes needed to meet minimal values (e.g., a p-value less than about 0.05) for statistical significance. Hence, what is considered an ideal number of genes will vary from condition to condition. When the biology is weaker, such as is the case typically with cosmetic condition phenotypes, fewer genes than those which may meet the statistical requisite for inclusion in the prior art, may be used to avoid adding noisy genes.

For example, the present inventors have determined that where gene expression profiling analysis of a skin condition yields from between about 2,000 and 4,000 genes having a statistical p-value of less than 0.05 and approximately 1000 genes having a p-value of less than 0.001, a very strong biological response is indicated. A moderately strong biological response may yield approximately 800-2000 genes have a statistical p-value of less than 0.05 combined with approximately 400-600 genes have a p-value of less than 0.001. In these cases, a gene expression signature comprising between about 100 and about 600 genes appears ideal. Weaker biology may be better represented by a gene expression signature comprising fewer genes, such as between about 20 and 100 genes.

While a gene expression signature may represent all significantly regulated genes associated with a skin condition of interest; typically it represents a subset of such genes. The present inventors have discovered that dandruff-related gene expression signatures comprising between about 100 and about 400 genes of approximately equal numbers of up-regulated and/or down-regulated genes are stable, reliable, and can provide predictive results. For example, a suitable gene expression signature may have from about 100-150 genes, 250-300 genes, 300-350 genes, or 350-400 genes. In a very specific embodiment, an unhealthy skin gene expression signature includes the 70 most up- and down-regulated genes. However, one of skill in the art will appreciate that gene expression signatures comprising fewer or more genes are also within the scope of the various embodiments of the invention. For purposes of depicting a gene expression signature, the probe set IDs associated with the genes are preferably separated into a first list comprising the most up-regulated genes and a second list comprising the most down-regulated, as set forth in FIG. 1A and FIG. 1B, Table B.

Gene expression signatures may be generated from full thickness skin biopsies from skin having the skin condition of interest compared to a control. For generation of dandruff gene expression signatures, biopsies are taken from dandruff-affected scalp skin and compared to non-dandruff affected scalp skin sampled from an anatomically comparable site in an unaffected subject. The present investigators determined that with respect to a subject suffering from any dandruff, even scalp skin that is free of dandruff lesions has a perturbed thematic profile.

In other embodiments of the present invention, a gene expression signature may be derived from a gene expression profiling analysis of keratinocyte cells treated with a benchmark skin-active agent, in particular an anti-dandruff agent, to represent cellular perturbations leading to improvement in the skin tissue condition treated with that benchmark skin agent, wherein the signature comprises a plurality of genes up-regulated and down-regulated by the benchmark skin agent in cells in vitro. As one illustrative example, microarray gene expression profile data where the perturbagen is the known anti-dandruff agent ZPT may be analyzed using the present invention to determine a subset of the most highly significantly regulated genes. Thus, a list of genes strongly up-regulated and strongly down-regulated in response to challenge with ZPT can be derived, and the list of genes (a proxy for the dandruff condition) can be used as a query signature to screen for anti-dandruff agents. In another embodiment, a signature may be derived to represent more than one aspect of the condition of interest.

In some embodiments a gene expression signature may be mapped onto a biological process grid or Gene Ontology, to yield a physiological theme pattern. The broadest pattern would include all themes where genes are statistically clustered. A more circumscribed pattern might include a subset of themes populated with the strongest-regulated genes, or a subset that is unique with respect to related disorders and therefore may provide a tool for differential diagnosis, or a tool for screening for actives having very precise and targeted effects. It will be clear that gene signatures derived from Gene Ontology and thematic pattern analysis will generally include fewer genes. An exemplary gene signature based on the lipid-immune/inflammation theme discovered by the present investigators as particularly relevant for dandruff is set forth in FIG. 1A and FIG. 1B, Table A.

Figure 6:
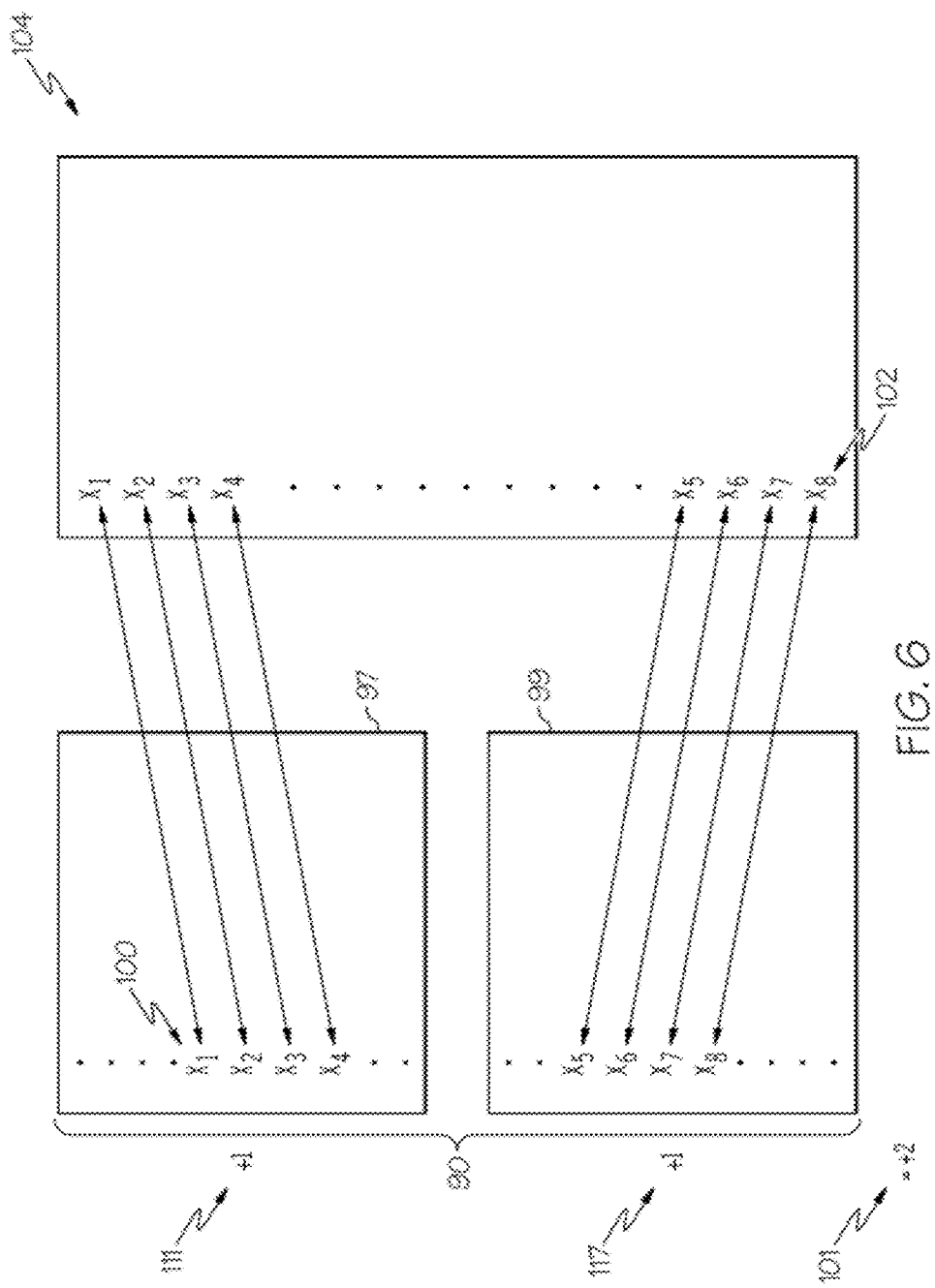
FIG. 6 is a schematic illustration of a comparison between a gene expression signature and an instance, wherein there is a positive correlation between the lists.
Figure 7:
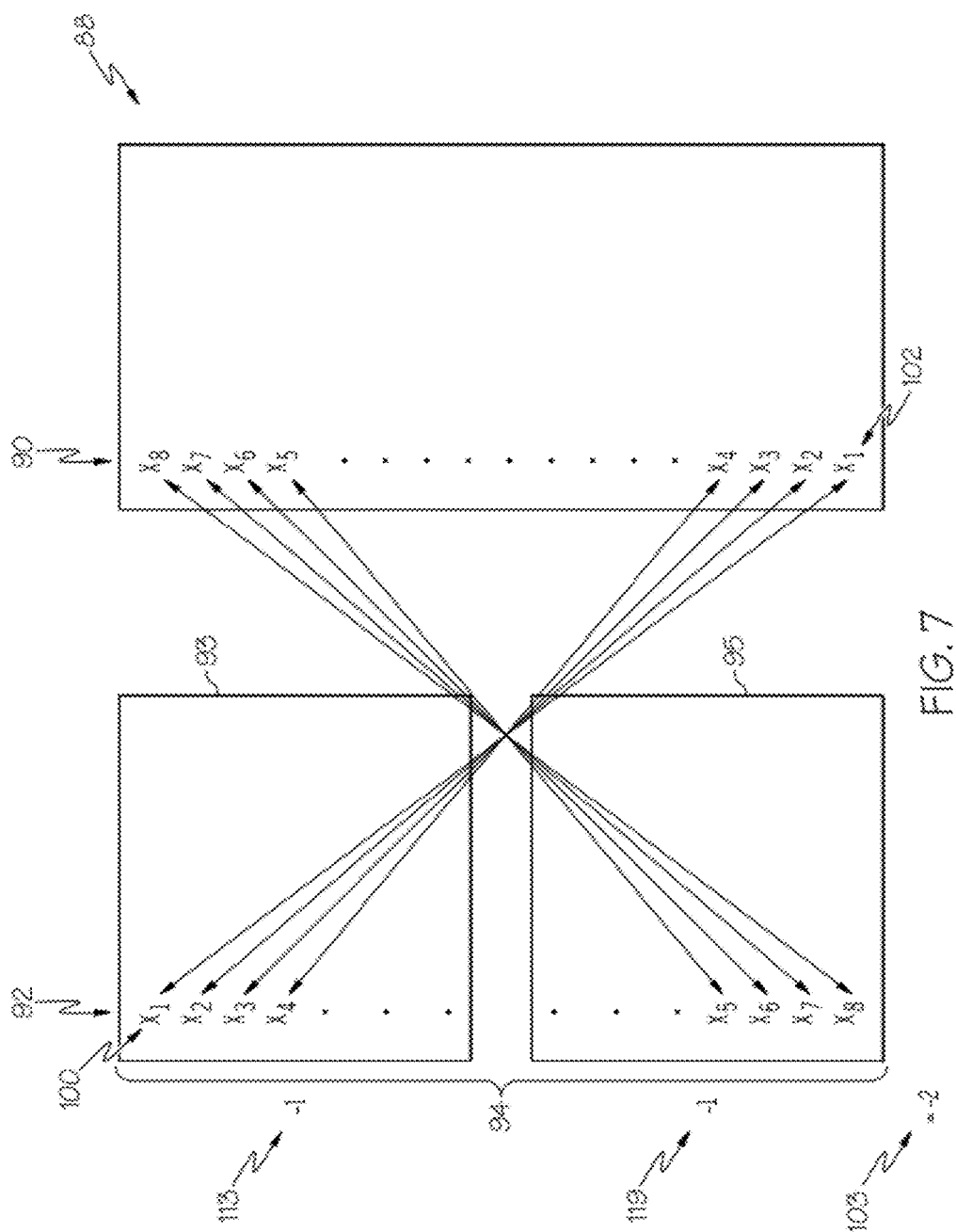
FIG. 7 is a schematic illustration of a comparison between a gene expression signature and an instance, wherein there is a negative correlation between the lists.
Figure 8:
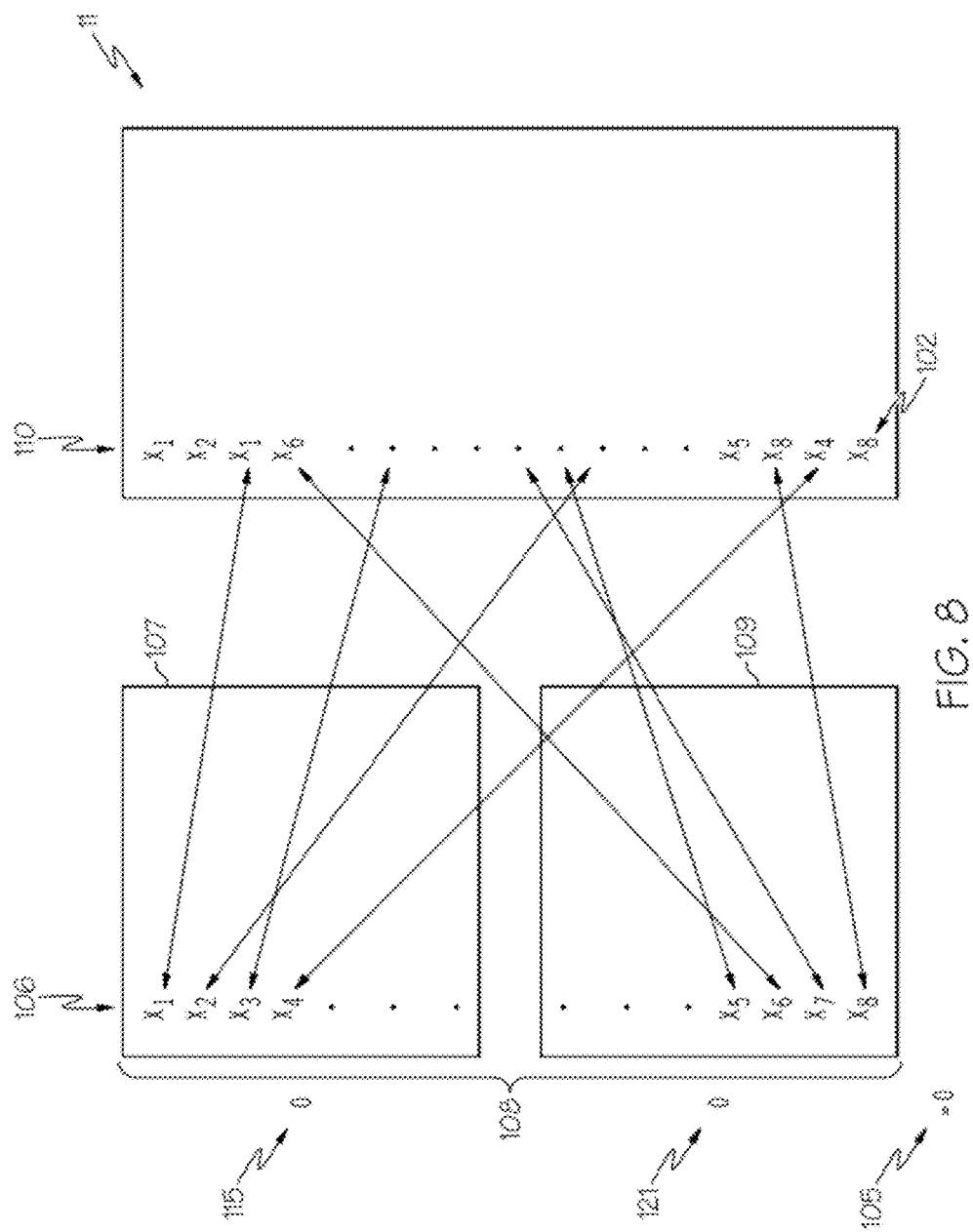
FIG. 8 is a schematic illustration of a comparison between a gene expression signature and an instance, wherein there is a neutral correlation between the lists.

IV. Methods for Comparing a Plurality of Instances to One or More Dandruff Gene Expression Signatures Referring to FIG. 6 and FIG. 7, a method for querying a plurality of instances with one or more dandruff gene signatures will now be described. Broadly, the method comprises querying a plurality of instances with one or more dandruff gene signatures and applying a statistical method to determine how strongly the signature genes match the regulated genes in an instance. Positive connectivity occurs when the genes in the up-regulated signature list are enriched among the up-regulated genes in an instance and the genes in the down-regulated signature list are enriched among the down-regulated genes in an instance. On the other hand, if the up-regulated genes of the signature are predominantly found among the down-regulated genes of the instance, and vice versa, this is scored as negative connectivity. FIG. 6 schematically illustrates an extreme example of a positive connectivity between signature 90 and the instance 104 comprising the probe IDs 102, wherein the probe IDs of the instance are ordered from most up-regulated to most down-regulated. In this example, the probe IDs 100 (e.g., $X_1$, $X_2$ $X_3$, $X_4$, $X_5$, $X_6$, $X_7$, $X_8$) of the gene signature 90, comprising an up list 97 and a down list 99, have a one to one positive correspondence with the most up-regulated and down-regulated probe IDs 102 of the instance 104, respectively. Similarly, FIG. 7 schematically illustrates an extreme example of a negative connectivity between signature 94 and the instance 88 comprising the probe IDs 90, wherein the probe IDs of the instance are ordered from most up-regulated to most down-regulated. In this example, the probe IDs of the up list 93 (e.g., $X_1$, $X_2$ $X_3$, $X_4$) correspond exactly with the most down-regulated genes of the instance 88, and the probe IDs of the down list 95 (e.g., $X_5$, $X_6$, $X_7$, $X_8$) correspond exactly to the most up-regulated probe IDs of the instance 88. FIG. 8 schematically illustrates an extreme example of neutral connectivity, wherein there is no consistent enrichment of the up- and down-regulated genes of the signature among the up- and down-regulated genes of the instance, either positive or negative. Hence the probe IDs 106 (e.g., $X_1$, $X_2$ $X_3$, $X_4$, $X_5$, $X_6$, $X_7$, $X_8$) of a gene signature 108 (comprising an up list 107 and a down list 109) are scattered with respect to rank with the probe IDs 110 of the instance 112, wherein the probe IDs of the instance are ordered from most up-regulated to most down-regulated. While the above embodiments illustrate process where the gene signature comprises both an up list and a down list representative of the most significantly up- and down-regulated genes of a skin condition, it is contemplated that the gene signature may comprise only an up list or a down list when the dominant biology associated with a condition of interest shows gene regulation in predominantly one direction.

In some embodiments, the connectivity score can be a combination of an up-score and a down score, wherein the up-score represents the correlation between the up-regulated genes of a gene signature and an instance and the down-score represents the correlation between the down-regulated genes of a gene signature and an instance. The up score and down score may have values between +1 and −1. For an up score (and down score) a high positive value indicates that the corresponding perturbagen of an instance induced the expression of the microarray probes of the up-regulated (or down-regulated) genes of the gene signature, and a high negative value indicates that the corresponding perturbagen associated with the instance repressed the expression of the microarray probes of the up-regulated (or down-regulated) genes of the gene signature. The up-score can be calculated by comparing each identifier of an up list of a gene signature comprising the up-regulated genes (e.g., Tables A, C, I and lists 93, 97, and 107) to an ordered instance list (e.g., Tables E, F, G, H) while the down-score can be calculated by comparing each identifier of a down list of a gene signature comprising the down-regulated genes (see, e.g., Tables B, D, J and down lists 95, 99, and 109) to an ordered instance list (e.g., Tables E, F, G, H). In these embodiments, the gene signature comprises the combination of the up list and the down list.

In some embodiments, the connectivity score value may range from +2 (greatest positive connectivity) to −2 (greatest negative connectivity), wherein the connectivity score (e.g., 101, 103, and 105) is the combination of the up score (e.g., 111, 113, 115) and the down score (e.g., 117, 119, 121) derived by comparing each identifier of a gene signature to the identifiers of an ordered instance list. In other embodiments the connectivity range may be between +1 and −1. Examples of the scores are illustrated in FIGS. 6, 7 and 8 as reference numerals 101, 103, 105, 111, 113, 115, 117, 119, and 121. The strength of matching between a signature and an instance represented by the up scores and down scores and/or the connectivity score may be derived by one or more approaches known in the art and include, but are not limited to, parametric and non-parametric approaches. Examples of parametric approaches include Pearson correlation (or Pearson r) and cosine correlation. Examples of non-parametric approaches include Spearman's Rank (or rank-order) correlation, Kendall's Tau correlation, and the Gamma statistic. Generally, in order to eliminate a requirement that all profiles be generated on the same microarray platform, a non-parametric, rank-based pattern matching strategy based on the Kolmogorov-Smirnov statistic (see M. Hollander et al. "*Nonparametric Statistical Methods*"; Wiley, New York, ed. 2, 1999)(see, e.g., pp. 178-185) can be used. It is noted, however, that where all expression profiles are derived from a single technology platform, similar results may be obtained using conventional measures of correlation, for example, the Pearson correlation coefficient.

In specific embodiments, the methods and systems of the present invention employ the nonparametric, rank-based pattern-matching strategy based on the Kolmogorov-Smirnov statistic, which has been refined for gene profiling data by Lamb's group, commonly known in the art as Gene Set Enrichment Analysis (GSEA) (see, e.g., Lamb et al. 2006 and Subramanian, A. et al. (2005) *Proc. Natl. Acad Sci U.S.A*, 102, 15545-15550). For each instance, a down score is calculated to reflect the match between the down-regulated genes of the query and the instance, and an up score is calculated to reflect the correlation between the up-regulated genes of the query and the instance. In certain embodiments the down score and up score each may range between −1 and +1. The combination represents the strength of the overall match between the query signature and the instance.

The combination of the up score and down score is used to calculate an overall connectivity score for each instance, and in embodiments where up and down score ranges are set between −1 and +1, the connectivity score ranges from −2 to +2, and represents the strength of match between a query signature and the instance. The sign of the overall score is determined by whether the instance links positivity or negatively to the signature. Positive connectivity occurs when the perturbagen associated with an instance tends to up-regulate the genes in the up list of the signature and down-regulate the genes in the down list. Conversely, negative connectivity occurs when the perturbagen tends to reverse the up and down signature gene expression changes, The magnitude of the connectivity score is the sum of the absolute values of the up and down scores when the up and down scores have different signs. A high positive connectivity score predicts that the perturbagen will tend to induce the condition that was used to generate the query signature, and a high negative connectivity score predicts that the perturbagen will tend to reverse the condition associated with the query signature. A zero score is assigned where the up and down scores have the same sign, indicating that a perturbagen did not have a consistent impact the condition signature (e.g., up-regulating both the up and down lists).

According to Lamb et al. (2006), there is no standard for estimating statistical significance of connections observed. Lamb teaches that the power to detect connections may be greater for compounds with many replicates. Replicating in this context means that the same perturbagen is profiled multiple times. Where batch to batch variation must be avoided, a perturbagen should be profiled multiple times in each batch. However, since microarray experiments tend to have strong batch effects it is desirable to replicate instances in different batches (i.e., experiments) to have the highest confidence that connectivity scores are meaningful and reproducible.

Each instance may be rank ordered according to its connectivity score to the query signature and the resulting rank ordered list displayed to a user using any suitable software and computer hardware allowing for visualization of data.

In some embodiments, the methods may comprise identifying from the displayed rank-ordered list of instances (i) the one or more perturbagens associated with the instances of interest (thereby correlating activation or inhibition of a plurality of genes listed in the query signature to the one or more perturbagens); (ii) the differentially expressed genes associated with any instances of interest (thereby correlating such genes with the one or more perturbagens, the skin tissue condition of interest, or both); (iii) the cells associated with any instance of interest (thereby correlating such cells with one or more of the differentially expressed genes, the one or more perturbagens, and the skin tissue condition of interest); or (iv) combinations thereof. The one or more perturbagens associated with an instance may be identified from the metadata stored in the database for that instance. However, one of skill in the art will appreciate that perturbagen data for an instance may be retrievably stored in and by other means. Because the identified perturbagens statistically correlate to activation or inhibition of genes listed in the query signature, and because the query signature is a proxy for a skin tissue condition of interest, the identified perturbagens may be candidates for new cosmetic agents, new uses of known cosmetic agents, or to validate known agents for known uses.

In some embodiments, the methods of the present invention may further comprise testing the selected candidate cosmetic agent, using in vitro assays and/or in vivo testing, to validate the activity of the agent and usefulness as a cosmetic agent. Any suitable in vitro test method can be used, including those known in the art, and most preferably in vitro models developed in accordance with the present invention. For example, MatTek human skin equivalent cultures or other skin equivalent cultures may be treated with one or a combination of perturbagens selected for mimicry of the skin condition of interest with respect to regulation of the genes constituting a physiological theme pattern for the skin condition of interest. The treated skin culture replicates the, for example, dandruff condition where it is treated with IL17 and IL22 in accordance with the instant invention, and perturbagens may be screened for their ability to shift the homeostatic equilibrium of the treated skin culture toward healthy skin, as determined by transcriptional analysis. Skin biopsy assays may also be used to evaluate candidate skin-active agents as anti-dandruff agents. In some embodiments, evaluation of selected agents using in vitro assays may reveal, confirm, or both, that one or more new candidate cosmetic agents may be used in conjunction with a known cosmetic agent (or a combination of known cosmetic agents) to regulate a skin condition of interest.

V. Methods for Developing In Vitro Models of Skin Disease Conditions

The present investigators discovered a novel application of C-map to derive in vitro models of skin disease conditions and to evaluate the sufficiency of in vitro or in vivo simulations of disease states.

A great challenge in the identification of new therapeutics is the development of in vitro models that are predictive of clinical efficacy. Because no animal models of the dandruff condition are available, there is a need for a model with high fidelity to the internal disease state so that it recapitulates the key features of dandruff lesional skin in vivo. The challenge of developing a good in vitro model for skin conditions such as dandruff is complicated by the fact that the events that trigger the development of dandruff are poorly understood. Transcriptomic profiling work in dandruff lesional skin has provided many new clues, chief among them evidence for a Th-17 driven inflammatory process. Without fully understanding how such a process is initiated in vivo, the present inventors surprisingly discovered that it is possible to simulate such a cascade in vitro by administering to skin cultures the key proinflammatory cytokines produced by Th-17 cells, IL-17A and IL-22.

Hence, it is possible to create an inflammatory milieu that resembles dandruff lesional skin. Indeed, investigation revealed that within four days of administration of human recombinant IL-22 and IL-17A into the culture medium of human 3-dimensional organotypic cultures, hyperplasia was produced, differentiation marker expression (e.g. K1/K10, S100A7) was perturbed, and secretion of IL-8 increased. All of these endpoints are features of dandruff lesional skin, and all substances that possess anti-dandruff activity in vivo are capable of blocking these responses in the novel in vitro model. These substances include selenium sulfide, ZPT, ketoconazole, clobetasol propionate and the iron chelator 1,10-phenanthroline.

The in vitro disease simulation according to the invention produces a pattern of gene expression that strongly resembles dandruff lesional skin. Affymetrix U133A Plus 2 microarrays were used to evaluate the gene expression profile elicited by exposure of organotypic human skin cultures to a variety of proinflammatory cytokines individually and in combination, as set forth in FIG. 21A and FIG. 21B. Analysis of Gene Ontology themes showed that the combination of IL-17A and IL-22 produces a thematic profile that closely resembles that of dandruff lesional skin, while other cytokines produced thematic profiles that were significantly different. Crucially, connectivity mapping exercises using gene expression signatures derived from dandruff lesional skin (e.g. "lipid-immune" and "dandruff" as set forth in FIG. 1A and FIG. 1B) show that this in vitro cytokine simulation produces linkages that are among the most strongly positively linked of all in the internal database which consists of ~5000 instances. This strongly supports that the simulation is producing a gene expression pattern that resembles the disease condition.

Connectivity mapping could be used to evaluate the sufficiency of other in vitro or even in vivo disease models in animals, including tr ansgenic animals (knockout, knock-in, etc.). The present investigators have demonstrated that by developing gene expression signatures from a disease state, it is possible using connectivity mapping to interrogate how closely a given disease model mimics the disease state. By manipulating model conditions to most closely approximate a disease state, predictivity of therapeutic efficacy is expected to be dramatically improved.

VI. Compositions and Personal Care Products

Generally, skin-active agents identified for the treatment of dandruff or dandruff-related skin conditions may be applied in accordance with cosmetic compositions and formulation parameters well-known in the art. Various methods of treatment, application, regulation, or improvement may utilize the skin care compositions comprising skin-active agents identified according to the inventive methods. The composition may be applied as part of routine hygiene relating to the hair and scalp and may be formulated as shampoos, conditioners, hair sprays, creams, ointments and the like. The composition may be applied to the scalp to treat dandruff or symptoms of dandruff present in other skin disorders.

U.S. Pat. Nos. 7,101,889; 5,624,666; 6,451,300; 6,974,569, and 7,001,594 are non-limiting examples of US patents comprising guidance on compositions, formulations, vehicles, administration, and other aspects relating to personal care products comprising anti-dandruff agents formulated for the treatment of dandruff. The entire disclosures of these patents are incorporated herein by this reference.

EXAMPLES

The present invention will be better understood by reference to the following examples which are offered by way of illustration not limitation.

Generally Applicable C-Map Methodology

Generating Instances

Individual experiments (referred to as batches) generally comprise 30 to 96 samples analyzed using Affymetrix GeneChip® technology platforms, containing 6 replicates of the vehicle control (e.g., DMSO), 2 replicate samples of a positive control that gives a strong reproducible effect in the cell type used, and samples of the test material/perturbagen. Replication of the test material is done in separate batches due to batch effects. In vitro testing was performed in 6-well plates to provide sufficient RNA for GeneChip® analysis (2-4 µg total RNA yield/well).

Human telomerized keratinocytes (tKC) were obtained from the University of Texas, Southwestern Medical Center, Dallas, Tex. tKC cells were grown in EpiLife® media with 1× Human Keratinocyte Growth Supplement (Invitrogen, Carlsbad, Calif.) on collagen I coated cell culture flasks and plates (Becton Dickinson, Franklin Lakes, N.J.). Keratinocytes were seeded into 6-well plates at 20,000 cells/cm$^2$ 24 hours before chemical exposure. Human skin fibroblasts (BJ cell line from ATCC, Manassas, Va.) were grown in Eagle's Minimal Essential Medium (ATCC) supplemented with 10% fetal bovine serum (HyClone, Logan, Utah) in normal cell culture flasks and plates (Corning, Lowell, Mass.). BJ fibroblasts were seeded into 6-well plates at 12,000 cells/cm$^2$ 24 hours before chemical exposure.

All cells were incubated at 37° C. in a humidified incubator with 5% $CO_2$. At t=-24 hours cells were trypsinized from T-75 flasks and plated into 6-well plates in basal growth medium. At t=0 media was removed and replaced with the appropriate dosing solution as per the experimental design. Dosing solutions were prepared the previous day in sterile 4 ml Falcon snap cap tubes. Pure test materials may be prepared at a concentration of 1-200 µM, and botanical extracts may be prepared at a concentration of 0.001 to 1% by weight of the dosing solution. After 6 to 24 hours of chemical exposure, cells were viewed and imaged. The wells were examined with a microscope before cell lysis and RNA isolation to evaluate for morphologic evidence of toxicity. If morphological changes were sufficient to suggest cytotoxicity, a lower concentration of the perturbagen was tested. Cells were then lysed with 350 µl/well of RLT buffer containing β-mercaptoethanol (Qiagen, Valencia, Calif.), transferred to a 96-well plate, and stored at -20° C.

RNA from cell culture batches was isolated from the RLT buffer using Agencourt® RNAdvance Tissue-Bind magnetic beads (Beckman Coulter) according to manufacturer's instructions. 1 µg of total RNA per sample was labeled using Ambion Message Amp™ II Biotin Enhanced kit (Applied Biosystems Incorporated) according to manufacturer's instructions. The resultant biotin labeled and fragmented cRNA was hybridized to an Affymetrix HG-U133A 2.0 GeneChip®, which was then washed, stained and scanned using the protocol provided by Affymetrix.

Example 1

Deriving a Dandruff Expression Signature

The samples were analyzed on the Affymetrix HG-U133 Plus 2.0 GeneChips, which contain 54,613 probe sets complementary to the transcripts of more than 20,000 genes. However, instances in the provided database used were derived from gene expression profiling experiments using Affymetrix HG-U133A 2.0 GeneChips, containing 22,214 probe sets, which are a subset of those present on the Plus 2.0 GeneChip. Therefore, in developing gene expression signatures from the clinical data, the probe sets were filtered for those included in the HG-U133A 2.0 gene chips.

A statistical analysis of the microarray data was performed to derive a plurality of dandruff gene expression signatures which may comprise a statistically relevant number of the up-regulated and down-regulated genes. In certain embodiments a dandruff gene expression signature includes between 10 and 400 up-regulated and/or between 10 and 400 down-regulated genes. In more specific embodiments a dandruff gene expression signature includes the 70 most statistically relevant up-regulated genes alone or in combination with the 70 most statistically relevant down-regulated genes. Regulation is determined in comparison to gene expression in normal dandruff-unaffected skin on non-dandruff subjects.

a. Filtering According to a Statistical Measure. For example, a suitable statistical measure may be p-values from a t-test, ANOVA, correlation coefficient, or other model-based analysis. As one example, p-values may be chosen as the statistical measure and a cutoff value of p=0.05 may be chosen. Limiting the signature list to genes that meet some reasonable cutoff for statistical significance compared to an appropriate control is important to allow selection of genes that are characteristic of the biological state of interest. This is preferable to using a fold change value, which does not take into account the noise around the measurements. The t-statistic was used to select the probe sets in the signatures because it is signed and provides an indication of the directionality of the gene expression changes (i.e. up- or down-regulated) as well as statistical significance.

b. Sorting the Probe Sets. All the probe sets are sorted into sets of up-regulated and down-regulated sets using the statistical measure. For example, if a t-test was used to compute p-values, the values (positive and negative) of the t-statistic are used to sort the list since p-values are always positive. The sorted t-statistics will place the sets with the most significant p-values at the top and bottom of the list with the non-significant ones near the middle.

c. Creation of the Gene Expression Signature. Using the filtered and sorted list created, a suitable number of probe sets from the top and bottom are selected to create a gene expression signature that preferably has approximately the same number of sets chosen from the top as chosen from the bottom. For example, the gene expression signature created may have at least about 10, 50, 70, 100, 200, or 300 and/or less than about 800, 600, 400 or about 100 genes corresponding to a probe set on the chip. The number of probe sets approximately corresponds to the number of genes, but most genes are represented by more than one probe set. It is understood that the phrase "number of genes" as used herein, corresponds generally with the phrase "number of probe sets."

For dandruff, one exemplary gene expression signature includes the 70 most significant up and 70 most significant down-regulated probe sets determined from comparing a dandruff-affected skin sample to a dandruff-unaffected skin sample, as set forth in Table B, FIG. 1A and FIG. 1B. Another exemplary gene expression signature is derived from the physiological thematic signature where genes derived from the gene cluster associated with one or more significant themes constitute a gene expression signature. A dandruff gene expression signature reflecting the lipid-immune/inflammation theme signature is set forth in Table A, FIG. 1A and FIG. 1B.

Example 2

This example illustrates that the complex dandruff condition may be represented by keratinocyte-based models and screening methods, and that gene expression profiles from keratinocytes and dandruff gene expression signatures can be used to reliably screen for candidate cosmetic agents for dandruff. The Example further illustrates the use of the gene expression profile to determine physiological thematic signatures useful for querying C-map to generate potential new skin-active agents and useful for screening skin active agents for anti-dandruff efficacy.

In accordance with methods of the invention, a broad gene expression profile for dandruff constituting the approximately 3,700 most-regulated genes was determined from comparing transcription data of dandruff-affected scalp skin to non-dandruff scalp skin. By analyzing the gene expression data in terms of Gene Ontology, a physiological theme profile is determined. This Example further illustrates that analysis of the Gene Ontology for dandruff when compared to other dandruff-related conditions yields a highly specific theme pattern. According to the inventive methods, skin-active agents may be screened for potential efficacy in the treatment of dandruff by selecting agents which act to shift the physiological theme signature toward that of healthy skin which signifies restoration of a desired state of homeostatic equilibrium characteristic of non-affected skin. The present investigators hypothesize that such an approach to new active discovery will yield treatments both effective and long-lasting.

To screen for anti-dandruff agents having strong skin activity, a gene expression signature was selected to comprise a subset of up-regulated and down-regulated genes representative of lipid metabolism and those representative of immune/inflammatory response, the two physiological themes constituting the most statistically salient thematic profile for dandruff. It is noted however that a subset of up-regulated and down-regulated genes representative of hyperproliferation could have also been used for the gene signature.

This signature was used to query a C-map database comprising gene expression profiles from fibroblast and keratinocyte cell lines exposed to a large number of different chemicals including the anti-dandruff agents ketoconazole, climbazole, clobetasol propionate, ZPT, and selenium sulfide. Each agent was tested at several concentrations. As shown in Table E, the highest-ranked results include clobetasol propionate, which is known to be the most effective anti-dandruff agent which acts by triggering strong skin activity. This result validates the effectiveness of the process. In addition, the highest-ranked results also include the anti-fungal agents ketoconazole and climbazole, suggesting that they may effective in treating dandruff by inducing skin effects, as well as anti-fungal effects. Moreover, that ZPT and selenium sulfide are not in the list of instances strongly linked to the gene signature suggests that their anti-dandruff properties may be related to other activities not addressed by this thematic signature.

The results shown in Table E also confirm the conclusion that gene expression profiles from keratinocyte cell lines (a proxy for the epidermis) are useful for screening of candidate cosmetic agents for dandruff. As can be seen, the highest-ranked results are in keratinocyte cell lines.

TABLE E

| Rank | Chip ID | Chemical | Cell Line | Concentration | Score |
|---|---|---|---|---|---|
| 1 | GSS128_Keto_10_24hr-80 | Ketoconazole | tKC | 10 µM | −0.72 |
| 2 | GSS128_CB_10_24hr-58 | Climbazole | tKC | 10 µM | −0.67 |
| 3 | GSS128_CP_20_24hr-67 | Clobetasol Propionate | tKC | 20 µM | −0.65 |
| 4 | GSS128_Keto_10_24hr-79 | Ketoconazole | tKC | 10 µM | −0.63 |
| 5 | GSS128_CP_10_24hr-66 | Clobetasol Propionate | tKC | 10 µM | −0.62 |
| 6 | GSS128_CB_20_24hr-60 | Climbazole | tKC | 20 µM | −0.61 |

TABLE E-continued

| Rank | Chip ID | Chemical | Cell Line | Concentration | Score |
|---|---|---|---|---|---|
| 7 | GSS128_Keto_1_24hr-78 | Ketoconazole | tKC | 1 µM | −0.58 |
| 8 | GSS128_CP_20_24hr-68 | Clobetasol Propionate | tKC | 20 µM | −0.57 |
| 9 | GSS128_CB_1_6hr-16 | Climbazole | tKC | 1 µM | −0.55 |
| 10 | GSS106A_cyclosporin_01_tert_keratinocytes | Cyclosporin | tKC | 10 µM | −0.54 |
| 11 | GSS128_CP_10_24hr-65 | Clobetasol Propionate | tKC | 10 µM | −0.54 |
| 12 | GSS122_MCF_Cyclosporin_B | Cyclosporin | MCF7 | 10 µM | −0.53 |
| 13 | GSS106A_triac_01_tert_keratinocytes | Triac | tKC | 10 µM | −0.53 |
| 14 | GSS128_CB_20_24hr-59 | Climbazole | tKC | 20 µM | −0.53 |
| 15 | 5202764005789148112904.C05 | Rosiglitazone | MCF7 | 10 µM | −0.51 |

In light of the above, it was concluded that the complex dandruff condition may be represented by keratinocyte-based models and screening methods. Moreover, it was determined that C-map, gene expression profiles from keratinocytes, and dandruff gene expression signatures can be used to reliably screen for candidate cosmetic agents for dandruff. Furthermore, it was determined that such screening can be done without knowing the mechanisms of action involved in dandruff.

Example 3

This Example illustrates validation of an In Vitro Model of the dandruff condition according to one embodiment of the present invention and the use of Thematic Signatures to guide the C-map query for skin-active agent candidate output.

Gene expression data from five inflammatory skin disorders (acne, atopic dermatitis, dandruff, eczema and psoriasis) were collected from a clinical genomics study and published studies. The raw expression data were used to produce a rank-ordered list of most differentially regulated genes associated with inflammatory skin disorders. This list was used to construct a gene signature for querying the provided database, the signature comprising the top 70 up-regulated and 70 down-regulated genes from the rank-ordered list.

The derived gene signature was used to query a provided database comprising gene expression data from clinical genomics studies of a widely different inflammatory skin disorders, published in vitro genomics studies of disparate inflammatory skin disorders, and genomics data from an internal in vitro model of dandruff inflammatory pathology (human organotypic, MatTek, cultures). As shown in Table F, the signature mapped strongly to the internal model, as well as to clinical genomics studies, thereby suggesting that the internal model elicits gene expression changes that are comparable to what is seen in vivo in inflammatory skin conditions. Thus, the internal model was validated as being useful for study of inflammatory cascades and other gene expression alterations associated with inflammatory skin disorders.

TABLE F

Connectivity Map Linkage Scores Using Derived Signature to Query the Database

| Rank | Chip ID | Treatment | Cell Line | Conc. | Score | Up Score | Down Score |
|---|---|---|---|---|---|---|---|
| 9428 | GSM173545-IL24 | IL24 | RHE | 20 ng/ml | 0.833 | 0.485 | −0.348 |
| 9427 | GSM173544-IL24 | IL24 | RHE | 20 ng/ml | 0.829 | 0.517 | −0.313 |
| 9426 | GSM173537-IL19 | IL19 | RHE | 20 ng/ml | 0.807 | 0.505 | −0.302 |
| 9425 | GSM173546-IL24 | IL24 | RHE | 20 ng/ml | 0.801 | 0.461 | −0.340 |
| 9424 | GSM173542-IL22 | IL22 | RHE | 20 ng/ml | 0.789 | 0.444 | −0.345 |
| 9423 | GSM173535-IL19 | IL19 | RHE | 20 ng/ml | 0.749 | 0.410 | −0.339 |
| 9422 | GSM173541-IL22 | IL22 | RHE | 20 ng/ml | 0.740 | 0.410 | −0.330 |
| 9421 | GSM173539-IL20 | IL20 | RHE | 20 ng/ml | 0.731 | 0.424 | −0.307 |
| 9420 | GSM173536-IL19 | IL19 | RHE | 20 ng/ml | 0.729 | 0.460 | −0.269 |
| 9419 | GSM173556-IL1b | IL1b | RHE | 10 ng/ml | 0.710 | 0.420 | −0.291 |
| 9418 | GSM173543-IL22 | IL22 | RHE | 20 ng/ml | 0.705 | 0.388 | −0.317 |
| 9417 | GSM173540-IL20 | IL20 | RHE | 20 ng/ml | 0.702 | 0.333 | −0.369 |
| 9416 | GSM173538-IL20 | IL20 | RHE | 20 ng/ml | 0.668 | 0.436 | −0.232 |
| 9415 | GSM173554-IFNg | IFNg | RHE | 10 ng/ml | 0.665 | 0.420 | −0.245 |
| 9414 | GSM173553-IFNg | IFNg | RHE | 10 ng/ml | 0.657 | 0.431 | −0.226 |
| 9413 | GSM173555-IL1b | IL1b | RHE | 10 ng/ml | 0.649 | 0.380 | −0.269 |
| 9412 | GSS157_13 | BEAS-2B RV-13 | BEAS-2B | | 0.602 | 0.378 | −0.224 |
| 9411 | GSM305449 | HK23/2 IL17 | hKC | 200 ng/ml | 0.579 | 0.428 | −0.151 |
| 9410 | GSM305450 | HK23/2 IL22 | hKC | 200 ng/ml | 0.573 | 0.358 | −0.214 |
| 9409 | GSM305448 | HK23/2 IFNg | hKC | 20 ng/ml | 0.552 | 0.450 | −0.102 |

Legend:
IL = interleukin;
IFN = interferon;
RHE = reconstituted human epidermis;
BEAS-2b RV-13 = Human Bronchial Epithelial Cells treated with rhinovirus-13;
hKC = human keratinocytes

Example 4

This example illustrates application of transcriptional profiling to investigate the pathogenesis of dandruff and to determine the mechanism of action of a benchmark anti-dandruff active.

Dandruff (seborrheic dermatitis) is a chronic keratinous condition and involves numerous variables and mechanisms, many of which are unknown. It is believed that dandruff has hereditary components and environmental components (e.g. yeast irritation). Most anti-dandruff research is directed to anti-fungal properties of agents rather than host-centric properties (i.e., inducement or reduction in a response in the human).

Dandruff and seborrheic dermatitis are common chronic relapsing scalp skin disorders that share some clinical features in common with psoriasis and atopic dermatitis. While seborrheic dermatitis can affect sebum-rich area other than scalp, we routinely refer to these conditions on the scalp collectively as "dandruff." Like psoriasis and atopic dermatitis, the pathogenesis of dandruff is complex, and appears to be the result of interactions among scalp skin, cutaneous microflora and the cutaneous immune system. The key clinical features of dandruff include flaking and itch, but the understanding of the precise underlying events that provoke these symptoms is limited.

Clues, however, have been derived from studies concerning the removal of *Malassezia* yeasts by treatment with antifungal drugs; studies involving treatment with corticosteroids or coal tar; as well as from investigations involving stratum corneum (SC) ultrastructure, and SC lipid composition. All of this evidence supports that there is a pronounced disruption of epidermal homeostasis that leads to the excessive scaling prominent in the dandruff condition. For example, the presence of parakeratosis in SC samples from the dandruff condition suggests that hyperproliferation is a feature of the dandruff lesion, and the associated puritis (itch) is possibly the result of inflammation and mast cell degranulation.

Generally, gene expression profiles in for the disease condition are compared to the gene expression profiles in the non-disease condition to determine genes differentially regulated in the condition, referred to as the gene expression profile. The profile is analyzed to determine the key physiological disruptions manifest in the condition. Once a physiological theme profile is derived for the condition, a C-map may be queried for perturbagens with strong connectivity to the relevant physiological themes. The goal is to identify a set of one or more perturbagens which when applied either alone or in combination to a skin culture, engender a response in the skin culture having a thematic signature which substantially mimics the thematic signature of the disease condition. The skin culture may then be used to screen for agents having strong negative connectivity to the thematic signature. The present inventors determined a physiological thematic signature for a dandruff condition, with the broad pattern set forth in FIG. 9. By Gene Ontology analysis and in accordance with Example 3, above, a highly relevant thematic signature for dandruff was derived which includes the themes of lipid metabolism and immune/inflammation in an inverse relationship. That is, in the dandruff condition the thematic signature includes a decrease in lipid metabolism with an increase in inflammation. In the following examples, gene expression signatures according to an aspect of the invention are used to investigate the skin response for a benchmark anti-dandruff agent, ZPT.

Methods

Two separate studies were performed:

1) 31 healthy male subjects aged 18-75 were divided into two groups of 16 "non-dandruff" and 15 "dandruff" subjects, as defined by a published flake scoring procedure, adherent scalp flake score (ASFS). Two full-thickness four-millimeter punch biopsies were obtained from the dandruff subjects, one at an actively flaking site "involved," and one from a non-flaking site "uninvolved." A single biopsy was collected from the non-sufferers at an anatomically comparable site.

2) In a double-blinded treatment study, 45 healthy male subjects (30 dandruff and 15 non-dandruff as defined by ASFS criteria, aged 18-50 years) were enrolled and were shampooed at the clinical site three (3) times a week for three (3) weeks with either a commercially available anti-dandruff shampoo with 1% ZPT (15 dandruff subjects) or the same formula without ZPT (15 dandruff and 15 non-dandruff subjects). Full thickness 2 mm biopsies were collected from all three groups at baseline and end of study. Total RNA was extracted from the biopsies and labeled for Affymetrix GeneChip® analysis. The synthesized target cRNA was hybridized to Affymetrix HG U133A microarrays. Statistically analyzed data were filtered by significance ($p<0.05$, Dandruff vs. Non-Dandruff; ZPT vs. vehicle treatments) to identify genes showing an increase or decrease in expression level, a standard bioinformatics approach.

Figure 10:
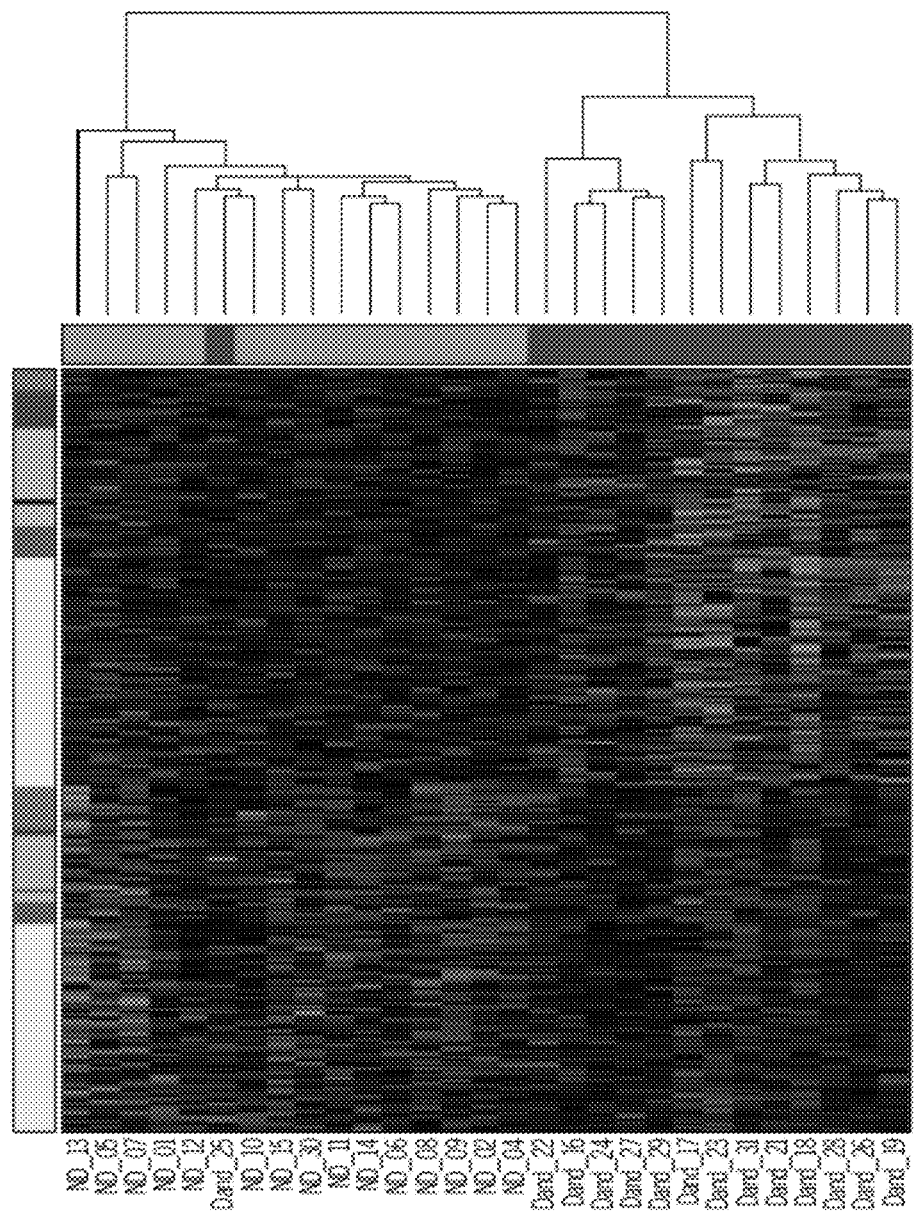
FIG. 10 depicts a heat map showing differential gene expression and theme analysis for dandruff versus non-dandruff affected skin.

Methodology and Results of Study 1:

FIG. 10 illustrates the differential gene expression observed in Dandruff vs. Non-Dandruff for all individuals.

Genome-wide transcriptional profiles were assessed using RNA extracted from full thickness scalp biopsies. Target cDNA (from extracted mRNA) was hybridized to Affymetrix U133 Plus 2 microarrays (54,613 probes). A heat map of normalized expression value (z-score) of significantly differentiated genes (3757) in expression between healthy (green) and dandruff (red) samples was generated.

At least one of Affymetrix probe sets for a given gene had a p-value of a t-test less than 0.05. A signal value of a probe set with the minimum p-value was used in the heat map. Looking at the heat map of FIG. 10, the column side bar indicates sample groups and the row side bar indicates biological processes in Gene Ontology. The color scheme for the biological process themes are: Green: Lipid metabolism; Red: Immune Response; Orange: Response to Stimulus; Blue: Epidermis Development; Cyan: Cell Proliferation; Magenta: Apoptosis; Yellow: Others. This color scheme applies to all heat maps set forth in the Figures herein.

Figure 11:
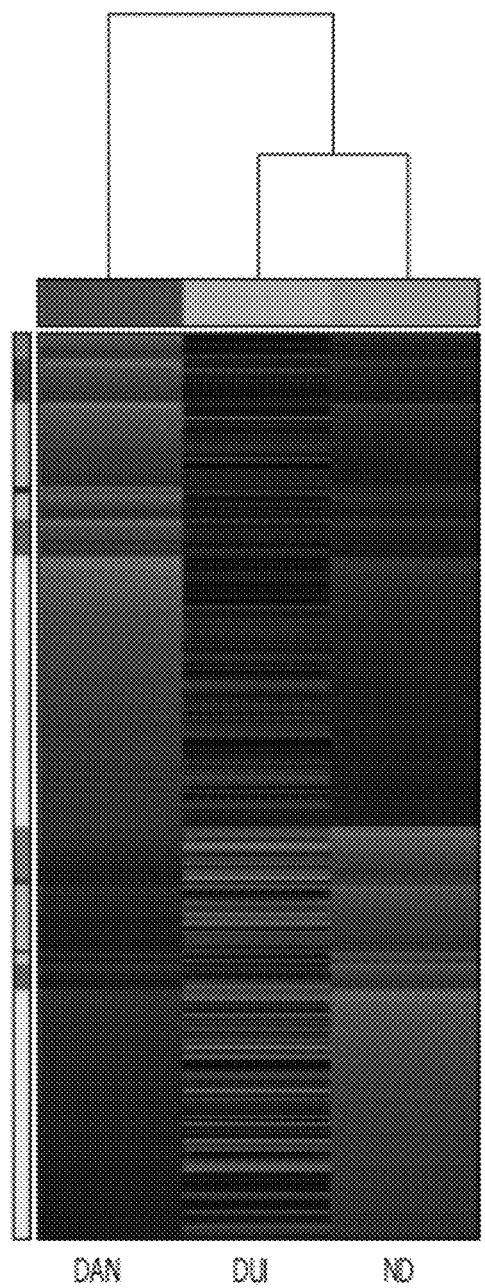
FIG. 11 depicts a heat map of the average normalized expression values of the significantly regulated genes in dandruff-involved, dandruff uninvolved and normal scalp skin versus biological processes in Gene Ontology.

Group averages for the same 3,757 genes as above are reflected in the heat map set forth in FIG. 11. The heat map depicts the averaged normalized expression values of the significantly differentiated genes in expression between dandruff and healthy scalp among each sample group. The column side bar indicates sample groups and the row side bar indicates biological processes in Gene Ontology. The investigators note that although dandruff uninvolved (DUI) and noninvolved (ND) cluster together, many genes involved in immune response are elevated in dandruff uninvolved skin (skin sampled from apparently unaffected scalp skin belonging to the same subject from which the dandruff-affected skin is sampled), including those involved in complement, response to stress, pathogens, cell signaling, etc. The broad pattern physiological theme profile is set forth in FIG. 9.

Figure 12:
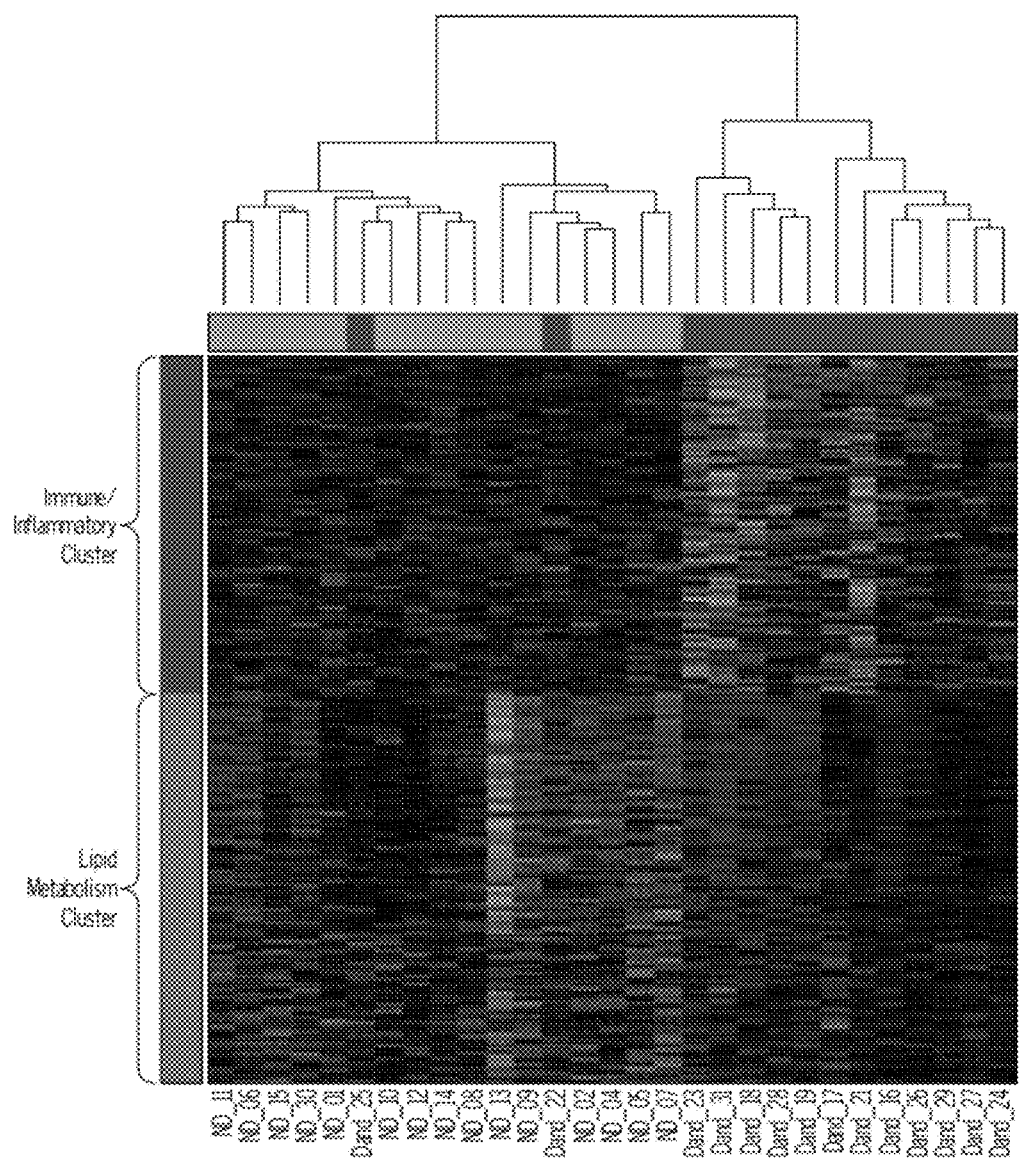
FIG. 12 depicts a heat map of differential gene expression in dandruff and non-dandruff conditions, specifically highlighting the inverse thematic relationship between lipid metabolism and Immune/inflammation.
Figure 13:
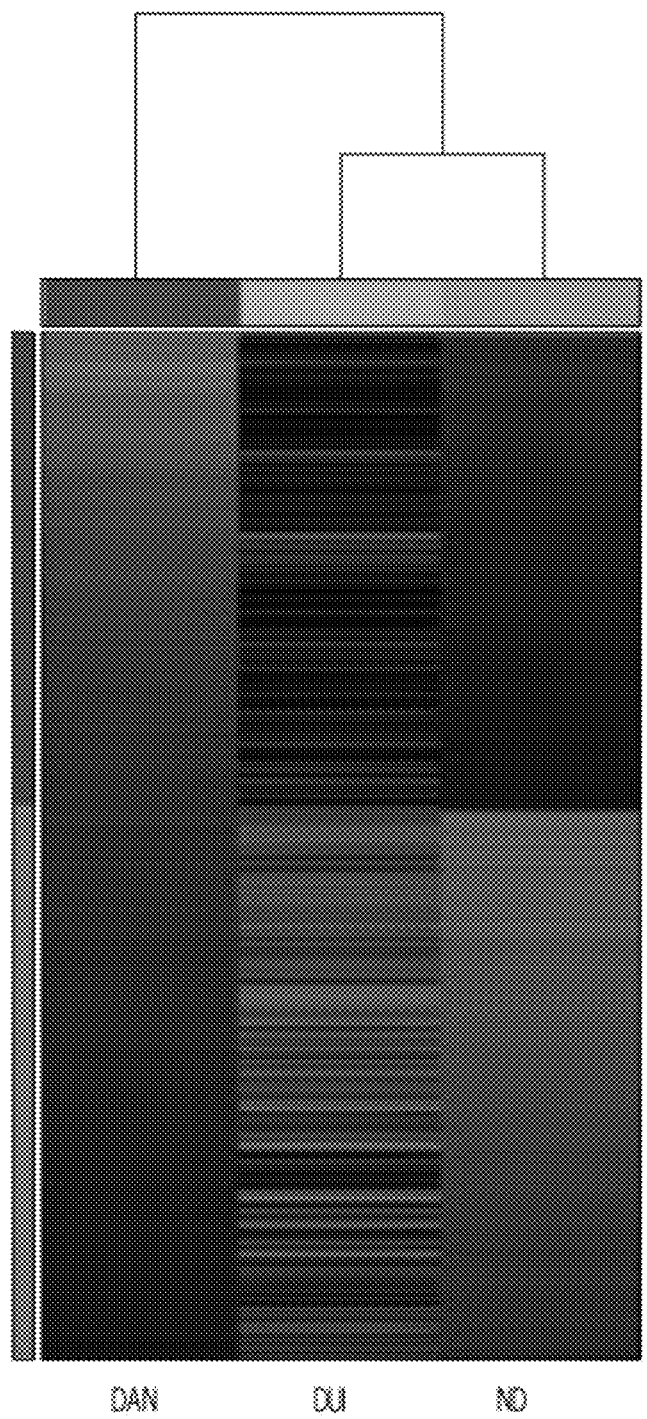
FIG. 13 depicts a heat map of differential gene expression between dandruff-affected, dandruff-uninvolved and non-dandruff conditions as group averages versus the lipid metabolism and immune/inflammatory thematic clusters.

A heat map depicting differential gene expression with respect to the more specific lipid metabolism/immune & inflammation theme signature for all individuals is set forth in FIG. 12. The columns are the subject descriptions, with non-dandruff grouped to the left and Dandruff to the right. The rows represent the Immune/Inflammatory cluster and the Lipid Metabolism cluster. Group averages for the data, including the subject conditions of dandruff-affected, dandruff-uninvolved and non-dandruff are set forth in FIG. 13.

Figure 14:
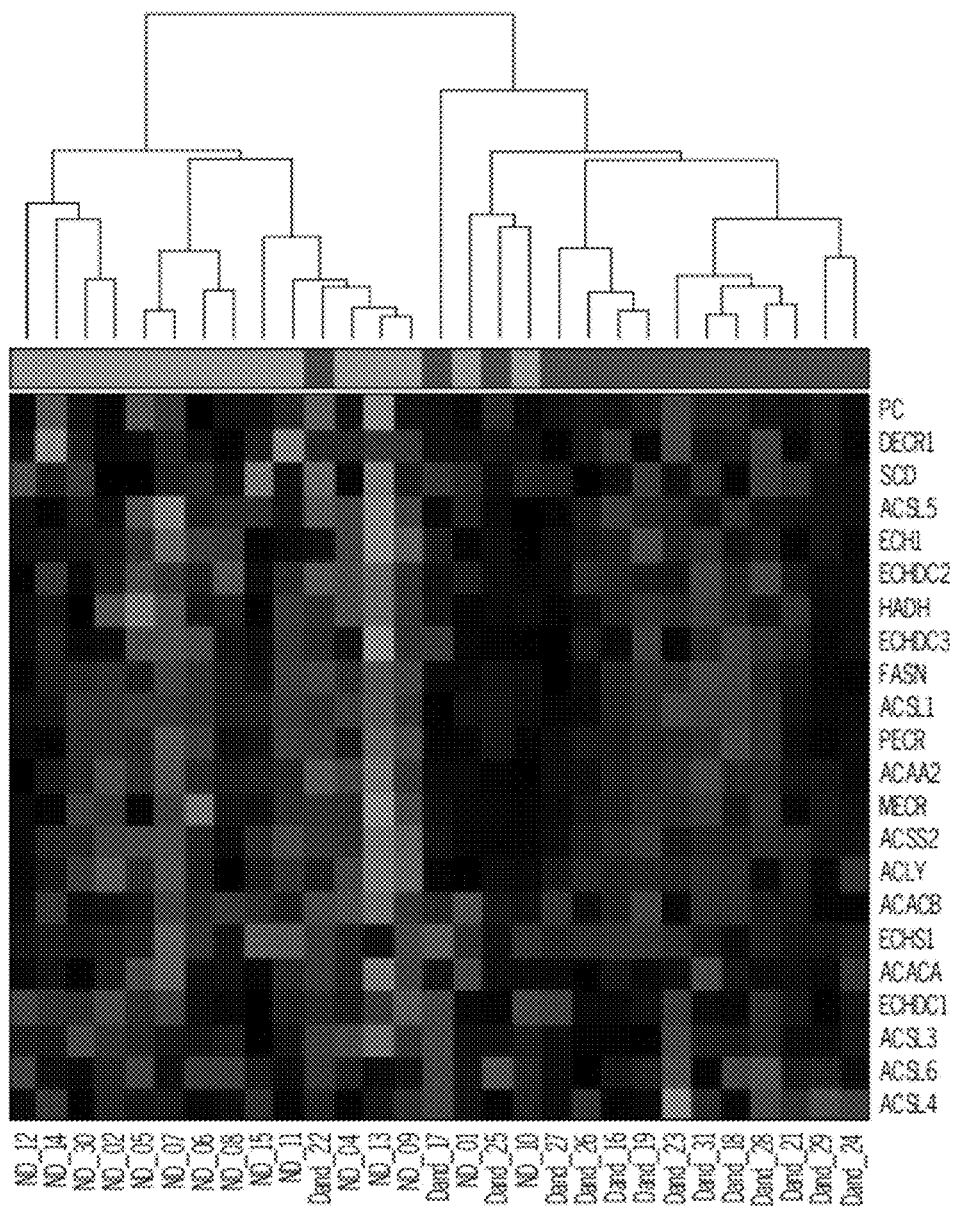
FIG. 14 illustrates the differential expression of genes involved in barrier lipid production, specifically the fatty acid synthetic pathway.
Figure 15:
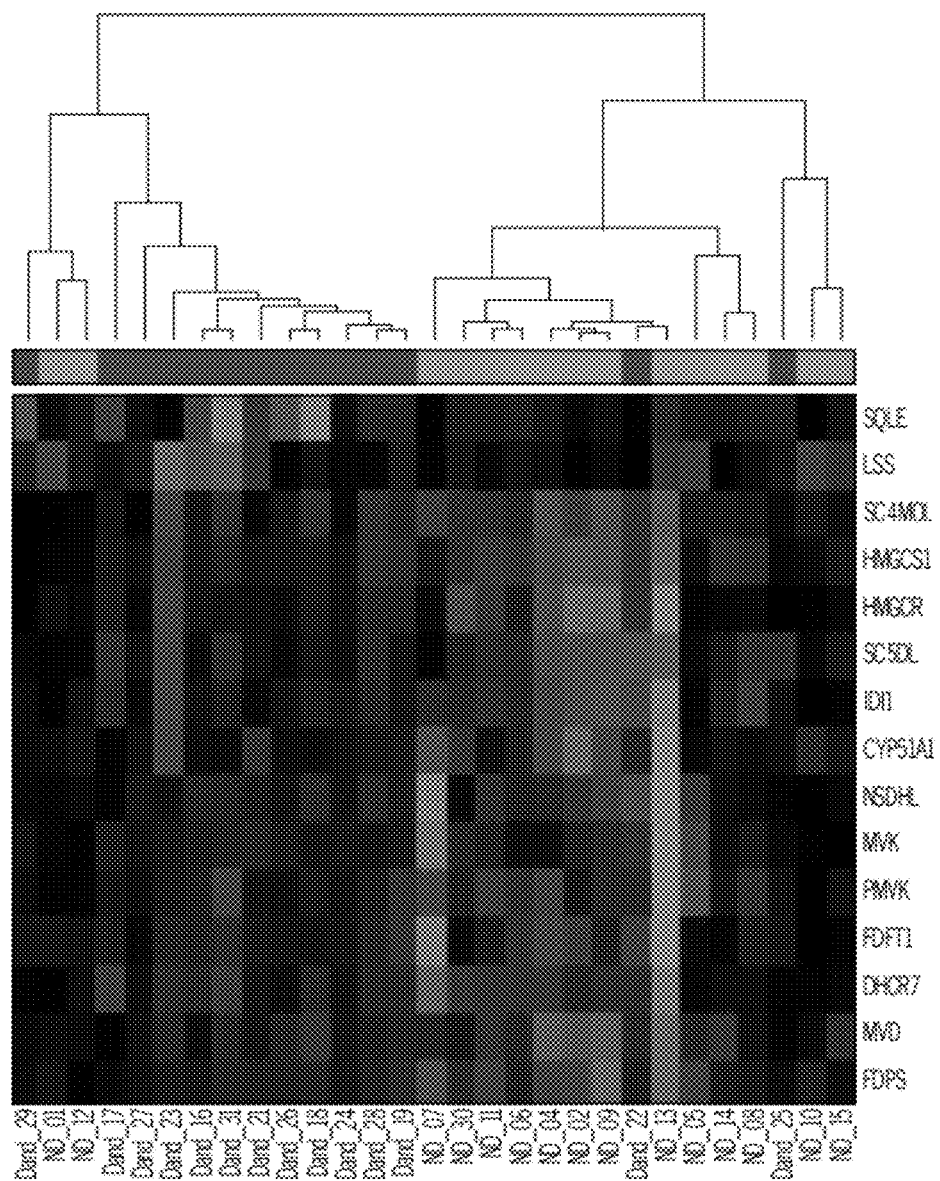
FIG. 15 illustrates the differential expression of genes involved in barrier lipid production, specifically the cholesterol synthetic pathway.
Figure 16:
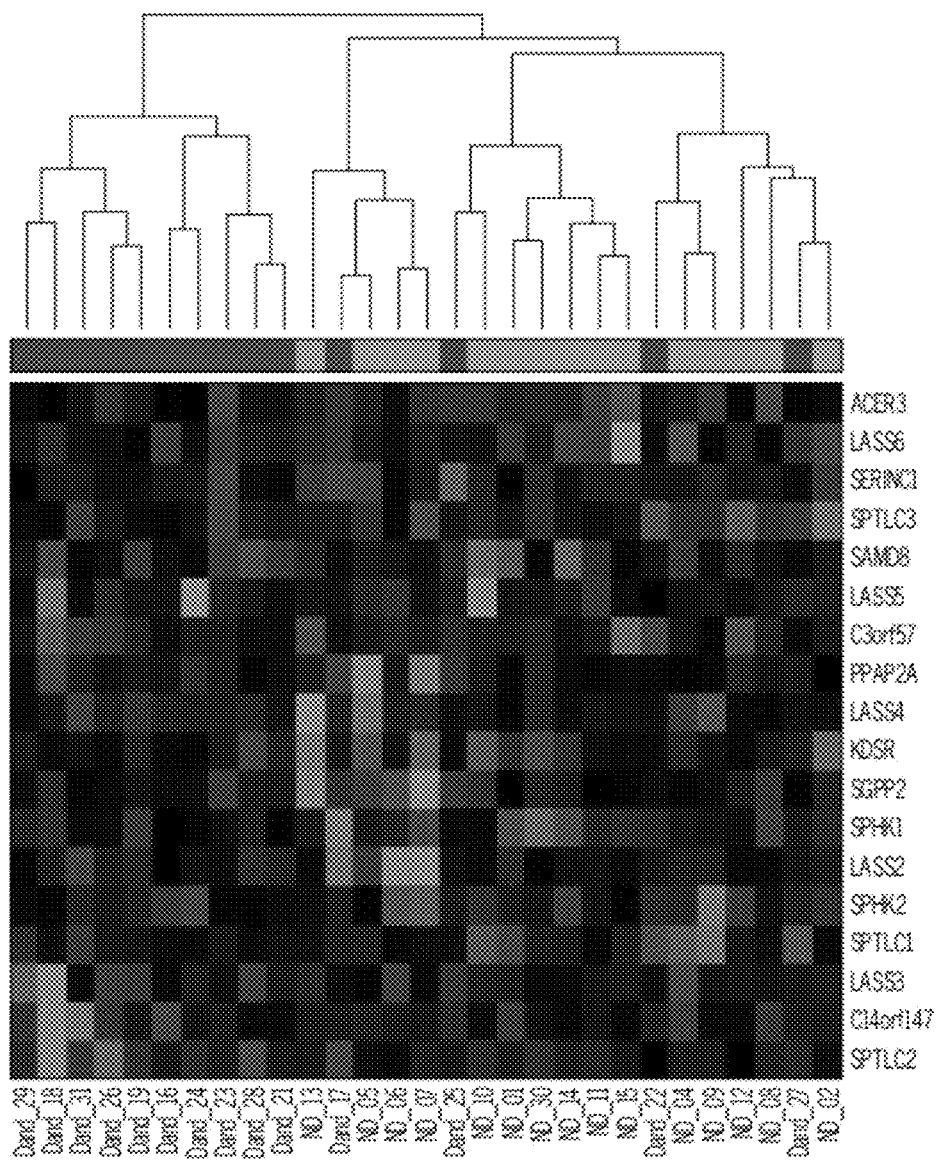
FIG. 16 illustrates the differential expression of genes involved in barrier lipid production, specifically the sphingolipid synthetic pathway.
Figure 17A:
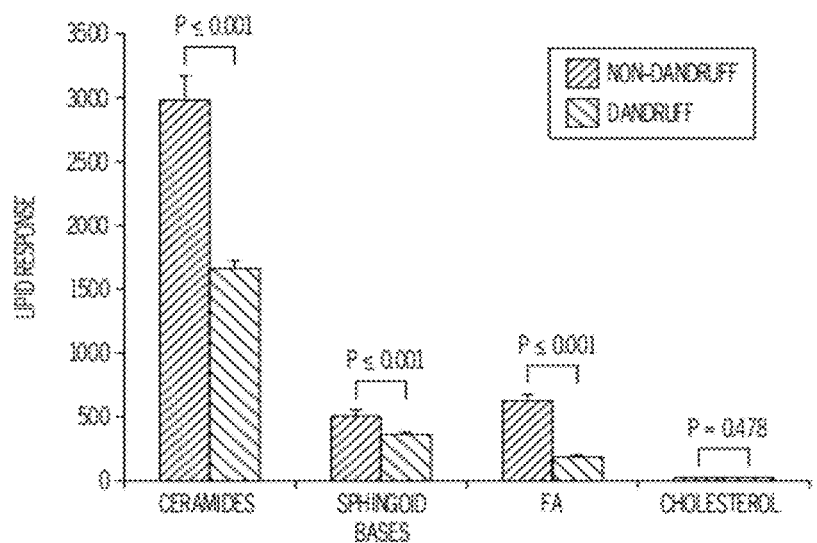
FIG. 17A and FIG. 17B sets forth data on barrier lipid and inflammatory biomarkers to illustrate phenotypic support for the transcriptomic findings.
Figure 17B:
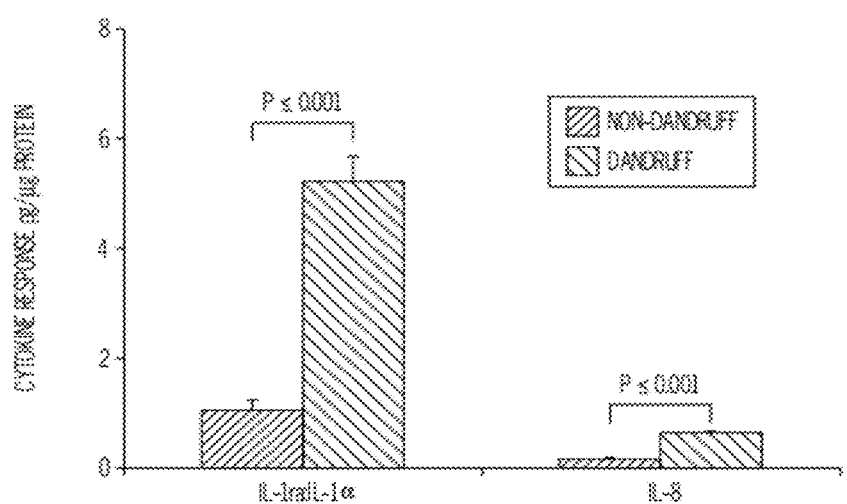

Heat maps depicting the differential expression of genes involved in skin barrier lipid production are set forth as FIG. 14 (Fatty acid synthesis pathway), FIG. 15 (cholesterol synthesis pathway) and FIG. 16 (sphingolipid synthesis pathway). This permits comparison with known stratum corneum biomarkers for these pathways. As set forth graphically in FIG. 17A and FIG. 17B, the biomarker data supports the transcriptomic findings with regard to the implication of barrier lipids and inflammation in the dandruff condition. Methodology, Results for Study 2:

The ZPT transcriptomics study design is set forth in FIG. 18. Notably, the study is a double-blind, vehicle-controlled evaluation of the effect of ZPT on scalp gene expression. The subject's hair/scalp was washed by study personnel on clinical site 3×/week for 3 weeks. Full thickness 2 mm punch biopsies collected at baseline and end of study. Product exposures were provided under conditions known to reliably reduce flake scores, epidermal thickness, itch and histamine, as well as substantially restore stratum corneum (SC) biomarker profiles.

Figure 19:
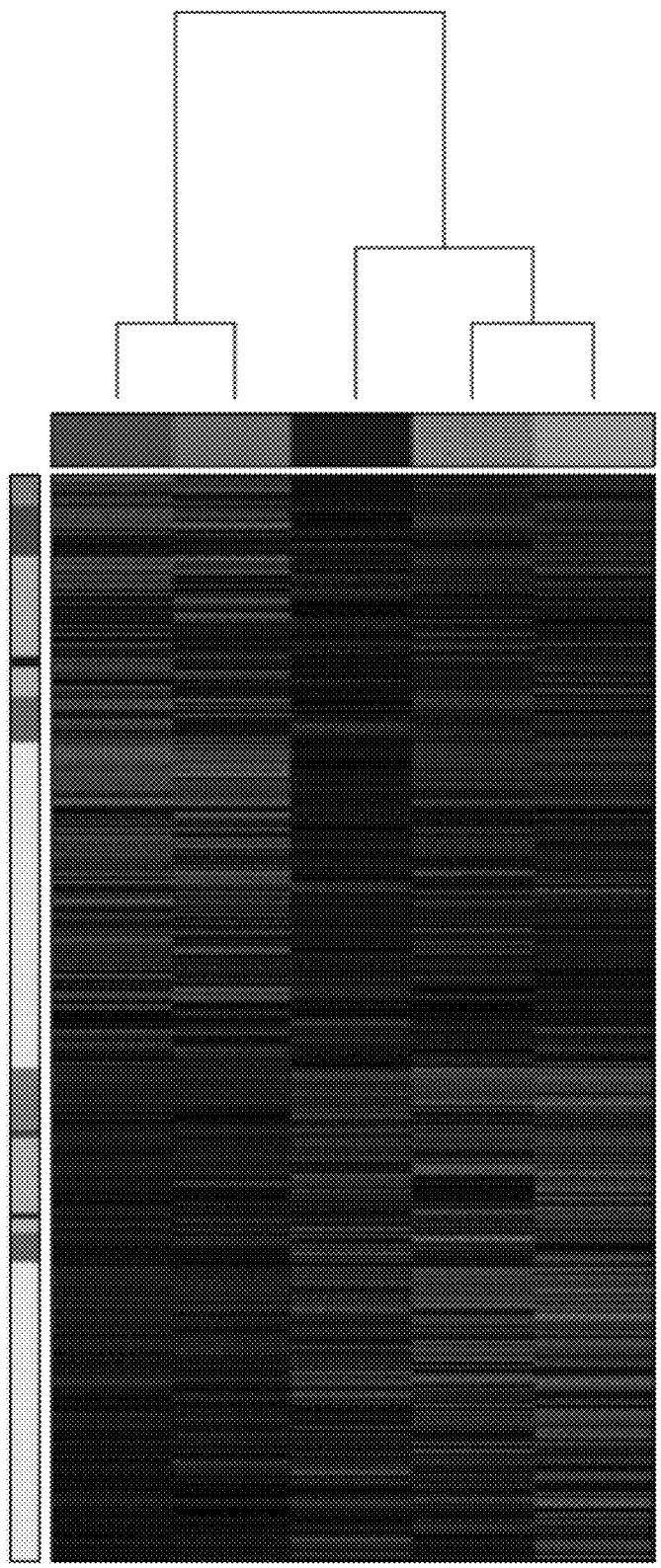
FIG. 19 depicts a heat map of ZPT treatment results demonstrating that treatment with ZPT results in a profile shift toward healthy scalp/homeostatic equilibrium.

The effect of ZPT treatment on differential gene expression is set forth for group averages as FIG. 19. As can clearly be seen by mere visual inspection, ZPT treatment at week 3 of the dandruff condition resulted in an expression shift toward the non-dandruff condition. The hierarchical clustering of ~3700 significantly altered genes shows that under conditions known to substantially resolve key symptoms, ZPT caused a dramatic change resulting in a broad profile that resembles healthy scalp.

FIG. 20 illustrates that the same result is seen where the gene expression signature is derived from the lipid/inflammation thematic model of the dandruff condition. Both for the lipid metabolism cluster and the immune/inflammation cluster, a dramatic shift toward the healthy scalp condition is suggested by inspection of the heat map.

The present investigators discovered through transcriptomic profiling of dandruff, dramatic alterations in a number of physiological processes, most notably an inverse thematic relationship between lipid metabolism and inflammation. Notably, the studies also show that genes involved in immune function/inflammation were statistically over-represented in the up-regulated category in a comparison of dandruff uninvolved skin and normal scalp, suggesting the existence of predisposing factors related to inflammation. The gene expression changes noted in the dandruff profile were substantially consistent at the phenotypic level (proteins and SC lipids). Treatment with a ZPT containing shampoo, but not the control without the active, was able to restore a transcriptomic profile that resembled that of healthy scalp skin (as shown by hierarchical clustering analysis).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for constructing a data architecture for use in identifying connections between perturbagens and genes associated with dandruff, and preparing a dandruff care composition comprising:
   (a) providing a gene expression profile for a control human epidermal keratinocyte cell;
   (b) generating a gene expression profile for a human epidermal keratinocyte cell exposed to at least one perturbagen, by extracting a biological sample from the treated cell and subjecting the biological sample to microarray analysis via a microarray scanner wherein generating the gene expression profile in at least one of
      (a) and (b) comprises
      i. isolating RNA from the human epidermal keratinocyte cell, and
      ii. creating cDNA from the isolated RNA;
   (c) identifying genes differentially expressed in response to the at least one perturbagen by comparing the gene expression profiles of (a) and (b);
   (d) creating an ordered list comprising identifiers representing the differentially expressed genes, wherein the identifiers are ordered according to the differential expression of the genes;
   (e) storing the ordered list as a keratinocyte instance on at least one computer readable medium; and
   (f) constructing a data architecture of stored keratinocyte instances by repeating (a) through (e), wherein the at least one perturbagen of step (a) is different qualitatively or quantitatively for each keratinocyte instance
   (g) querying the data architectures of stored keratinocyte instances with at least one dandruff gene expression signature, wherein querying comprises comparing the at least one dandruff gene expression signature to each stored keratinocyte instance, wherein the dandruff gene expression represents genes differentially expressed in association with dandruff;
   (h) assigning a connectivity score to each of the instances; and
   (i) preparing a dandruff care composition comparing at least one perturbagen, wherein the connectivity score of the instance associated with the at least one perturbagen has a negative correlation.

2. A method according to claim 1, comprising using a programmable computer to perform one or more of steps (c), (d), (e) and (f).

3. A method according to claim 1, wherein the ordered list comprises the ordered list of identifiers in association with a numerical ranking for the identifier corresponding to its rank in the ordered list.

4. A method according to claim 1, wherein the biological sample comprises mRNA.

5. A method according to claim 1, wherein the microarray is a global microarray or a specific microarray, wherein the specific microarray comprises oligonucleotides which hybridize to genes corresponding to a gene expression signature for a cellular phenotype.

6. A method according to claim 1, wherein the step of constructing the data architecture of stored keratinocyte instances by repeating steps (a) through (e) comprises repeating steps (a) through (e) for between about 50 and about 50,000 instances.

7. A method according to claim 6, wherein the step of constructing the data architecture of stored keratinocyte instances comprises repeating steps (a) through (e) for between about 1000 and about 20,000 instances.

8. A method according to claim 1, wherein the at least one perturbagen is an anti-dandruff agent.

9. A method according to claim 8, wherein the anti-dandruff agent induces a host response to produce a host effect, or induces anti-fungal activity to produce an anti-fungal effect, or both.

10. The method according to claim 9, wherein the anti-dandruff agent induces a host response to produce a host effect.

11. The method according to claim 10, wherein the host response is restoration of epidermal homeostasis present in healthy scalp skin.

12. The method according to claim 11, wherein restoration of epidermal homeostasis is assessed by measuring a shift in a transcriptional profile derived from scalp skin of the host toward a transcriptional profile of healthy scalp skin.

13. A method according to claim 1, wherein the identifiers are selected from the group consisting of gene names, gene symbols, microarray probe set ID values, and combinations thereof.

14. A method according to claim 1, wherein the ordered list is arranged so that an identifier associated with a most up-regulated gene is positioned at the top of the ordered list and an identifier associated with a most down-regulated gene is positioned at the bottom of the ordered list.

15. A method according to claim 14, wherein the ordered list of each keratinocyte instance is arranged so that an identifier associated with each gene that is not differentially expressed is positioned between the identifier associated with the most up-regulated gene and the identifier associated with the most down-regulated gene.

16. A method according to claim 1, wherein each keratinocyte instance comprises between about 1,000 and about 50,000 identifiers.

17. A method according to claim 1, wherein each keratinocyte instance comprises metadata for the at least one perturbagen associated with the instance.

18. A method according to claim 1, wherein at least one perturbagen is an anti-fungal agent.

19. A method according to claim 18, wherein an anti-fungal agent comprises zinc pyrithione (ZPT), selenium sulfide or both.

20. A method according to claim 1, wherein at least one perturbagen comprises an environmental stimuli.

21. The method according to claim 10 wherein the host response comprises one or more of inducing lipid metabolism, suppressing inflammation, suppressing cell proliferation, suppressing cell apoptosis and normalizing cell differentiation.

22. The method according to claim 21, wherein the host response comprises inducing lipid metabolism and suppressing inflammation.

* * * * *